US012714872B1

(12) United States Patent
Wessels

(10) Patent No.: US 12,714,872 B1
(45) Date of Patent: Aug. 25, 2026

(54) ROTATING ELECTRIC FIELD THERAPY FOR ALTERING BIOLOGIC TISSUE FUNCTION

(71) Applicant: Richard Joseph Wessels, Scandia, MN (US)

(72) Inventor: Richard Joseph Wessels, Scandia, MN (US)

( * ) Notice: Subject to any disclaimer, the term of this patent is extended or adjusted under 35 U.S.C. 154(b) by 0 days.

(21) Appl. No.: 19/233,909

(22) Filed: Jun. 10, 2025

Related U.S. Application Data

(60) Provisional application No. 63/731,798, filed on Jun. 10, 2024.

(51) Int. Cl.
*A61N 1/40* (2006.01)
*A61B 18/00* (2006.01)

(52) U.S. Cl.
CPC ........ *A61N 1/40* (2013.01); *A61B 2018/0022* (2013.01)

(58) Field of Classification Search
None
See application file for complete search history.

(56) References Cited

U.S. PATENT DOCUMENTS

2006/0167499 A1* 7/2006 Palti ........................ A61N 1/40 607/2
2020/0022653 A1* 1/2020 Moisa ................ A61B 18/1492
2020/0205892 A1* 7/2020 Viswanathan ..... A61B 18/1492
2022/0249854 A1* 8/2022 Ballard .............. A61N 1/39046
2025/0049490 A1* 2/2025 Schuler .................. A61B 18/02
2025/0281655 A1* 9/2025 Kaiser .................... G16H 40/63

* cited by examiner

*Primary Examiner* — Unsu Jung
*Assistant Examiner* — Sefra D. Manos
(74) *Attorney, Agent, or Firm* — Schwegman Lundberg & Woessner, P.A.

(57) ABSTRACT

Electrical medical therapy systems, devices, and methods can employ "electrodes" that are galvanically isolated from target biologic tissue. An electric field can be generated in the biologic tissue via such electrically insulated and galvanically isolated electrodes. Further the electric field can be directionally varied, such as to form a Rotating Electric Field (REF), such that it can impact biological cells from different directions. Directional variation of the electric field can be obtain using a set of three (triad) or more electrodes, or multiple such sets or triads, and applying respective phase-delayed time-varying electric signals to corresponding individual electrodes in the triad or other set of galvanically isolated electrodes. Medical electrical REF therapies can include, among other things, at least one of cardioversion, defibrillation, pacing or other cardiac resynchronization, ablation, cautery, vessel sealing, or thermal sterilization.

17 Claims, 34 Drawing Sheets

ROTATING FIELD
201
202
203
204
0-DEGREE FIELD ORIENTATION. TIME t=0 T

ROTATING FIELD
201
202
203
204
45-DEGREE FIELD ORIENTATION TIME t= (1/8) T

ROTATING FIELD
201
202
203
204
90-DEGREE FIELD ORIENTATION. TIME t= (2/8) T

GRAPHIC SHOWING CROSS SECTION OF HEART MUSCLE AND DISTINCT LAYERS OF MYOCARDIAL CELLS

GRAPHIC SHOWING TOP LEVEL REPRESENTATION OF CELLULAR ORIENTATIONS IN THE MYOCARDIAL LAYERS

REF ELECTRODE CONCEPT. GENERAL AND IDEAL CONFIGURATIONS

REF OVERLAYED SIGNALS

REF VECTOR ANALYSIS OF ROTATING FIELD

DETAILS OF DELAYS FOR GENERATING BASIS REF SINUSOIDAL SIGNALS – IDEAL QAUILATERAL ELECTRODE LAYOUT

DETAILS OF DELAYS FOR GENERATING BASIC REF SINUSOIDAL SIGNALS – GENERAL ELECTRODE LAYOUT.

BASIC TIME DELAYED SINUSOIDAL SIGNALS

DETAILS SHOWING SWITCH POINTS IN TIME DELAYED REF SIGNALS.

REF GENERATOR: ANALOG SUBSYSTEM – PART A

REF DIGITAL SUBSYSTEM

REF BALLOON CATHETER

REF ELECTRODES ON BALLOON. GENERAL CONCEPT

TRIPLE ELECTRODE GROUPED TO FORM APPLICATION TOOL.

TRIADS PLACED ON ANNULAR STRUCTURE.

THERAPY CYLINDER - LONGITUDINAL

THERAPY CYLINDER - ANNULAR & ONGITUDINAL

CROSS SECTION OF BALLOON BASED TRIAD RING – INSULATING LAYERS.

CROSS SECTION OF BALLOON BASED
TRIAD RING – INSULATING COATINGS.

ARTICULATED REF STRUCTURE - MULTIPLE LAYERED.

REF ELECTRODE CONFIGURATION WITH CLEAR TREATMENT AREA

DUAL BAND - DUAL DRIVER

DUAL BAND - SINGLE DRIVE

TRADITIONAL IPG AND LEAD PLACEMENT IN CARDIAC SYSTEM

REF TRIAD FOR AIMD - 2 LEADS

REF TRIAD FOR AIMD - 3 LEADS

REF TRIAD FOR AIMD - 1 LEAD AND CAN

REF TRIAD FOR AIMD - 2 LEADS AND CAN

THREE ELECTRODE REF LEAD

STRUCTURE OF TWO ELECTRODE REF LEAD

SUB-Q ICD

ROTATING FIELD VECTOR IN SUB-Q ICD

SENSORS AND DATA LINKAGE

EXTERNAL REF DEFIBRILLATION JACKET.

POSITIONING AND INCORPORATION OF ELECTRODE IN VEST MATERIAL

ROTATING ELECTRIC FIELD THERAPY FOR ALTERING BIOLOGIC TISSUE FUNCTION

CLAIM OF PRIORITY

This patent application claims the benefit of priority of Richard J. Wessels U.S. Provisional Patent Application Ser. No. 63/731,798, entitled "ROTATING ELECTRIC FIELD THERAPY (REF) FOR ALTERING BIOLOGIC TISSUE FUNCTION," filed on Jun. 10, 2024, which is hereby incorporated by reference herein in its entirety.

TECHNICAL FIELD

This document pertains generally, but not by way of limitation, to electrical medical therapy and more particularly, but not by way of limitation to a rotating electric field therapy for altering biologic tissue function.

BACKGROUND

Certain electrical medical treatments of tissue can employ electrodes directly galvanically contacting tissue, such as to deliver therapy. This can involve delivering bulk current through the tissue that is galvanically contacted, which can consume power, and which can have secondary effects to the therapy that are not necessary or even undesirable.

SUMMARY/OVERVIEW

This document describes, among other things, electrical medical therapy that can employ "electrodes" that are overlaid by an electrical insulator, such that no galvanic contact with the biologic tissue is made. Instead, an electric field can be generated in the biologic tissue via such electrically insulated and galvanically isolated electrodes. Further the electric field can be directionally varied, such as to form a Rotating Electric Field (REF), such that it can impact biological cells from different directions. Directional variation of the electric field can be obtain using a set of three (triad) or more electrodes, or multiple such sets or triads, and applying respective phase-delayed time-varying electric signals to corresponding individual electrodes in the triad or other set of galvanically isolated electrodes. Medical electrical REF therapies can include, among other things, at least one of cardioversion, defibrillation, pacing or other cardiac resynchronization, ablation, cautery, vessel sealing, or thermal sterilization.

The present rotating electric field (REF) therapy can employ time-delayed or otherwise temporally offset AC signals that can respectively be applied to individual ones multiple REF electrodes that are electrically galvanically isolated from targeted biologic tissue to generate a rotating electric field in the biologic tissue. The REF can have a main vector that changes the direction in which it points, such as by sweeping through a 360-degree two-dimensional space. This REF can be imposed of sufficient amplitude such that it alters the function of the biologic tissue, such as for example can include cardiac tissue, either on an acute or chronic basis, while minimizing energy used and minimizing impact to nearby organs and tissues.

Altering biologic tissue function, as in the case of defibrillation, can be achieved by applying the REF at electric field levels that are sufficiently high to stimulate the tissue (e.g., to interrupt the arrhythmia pathways in the tissue) but below levels that may cause permanent impact damage to the tissue, if that is the desired goal. However, the applied REF can be increased in energy, such as by increasing the amplitude to such a level that can achieve durable or permanent alteration of the tissue, such where cardiac or other tissue ablation is desired, such as to alter or totally deactivate the offending tissue that was responsible for initiating cardiac arrythmias.

With a rotating field, the entire circumference of the cells can be exposed to and affected by a perpendicular electric field as the REF rotates through 360 degrees. This can be especially effective for tissues in which the cells are oriented in multiple directions. Rotating the electric field can help ensure that more of the tissue is captured for the desired treatment (e.g., defibrillation, ablation, etc.) at lower energy levels.

This Summary/Overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figures 1A, 1B, 1C:
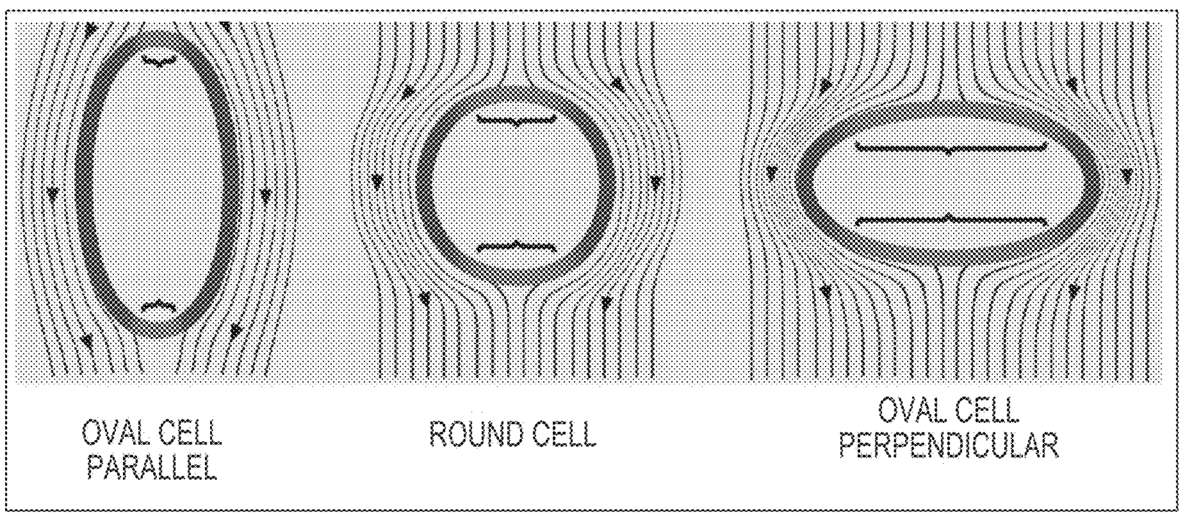
FIGS. 1A, 1B, and 1C are schematic diagrams of electric field lines about a cell that conceptually show cell geometry and electric field orientation.
Figures 2A, 2B, 2C:
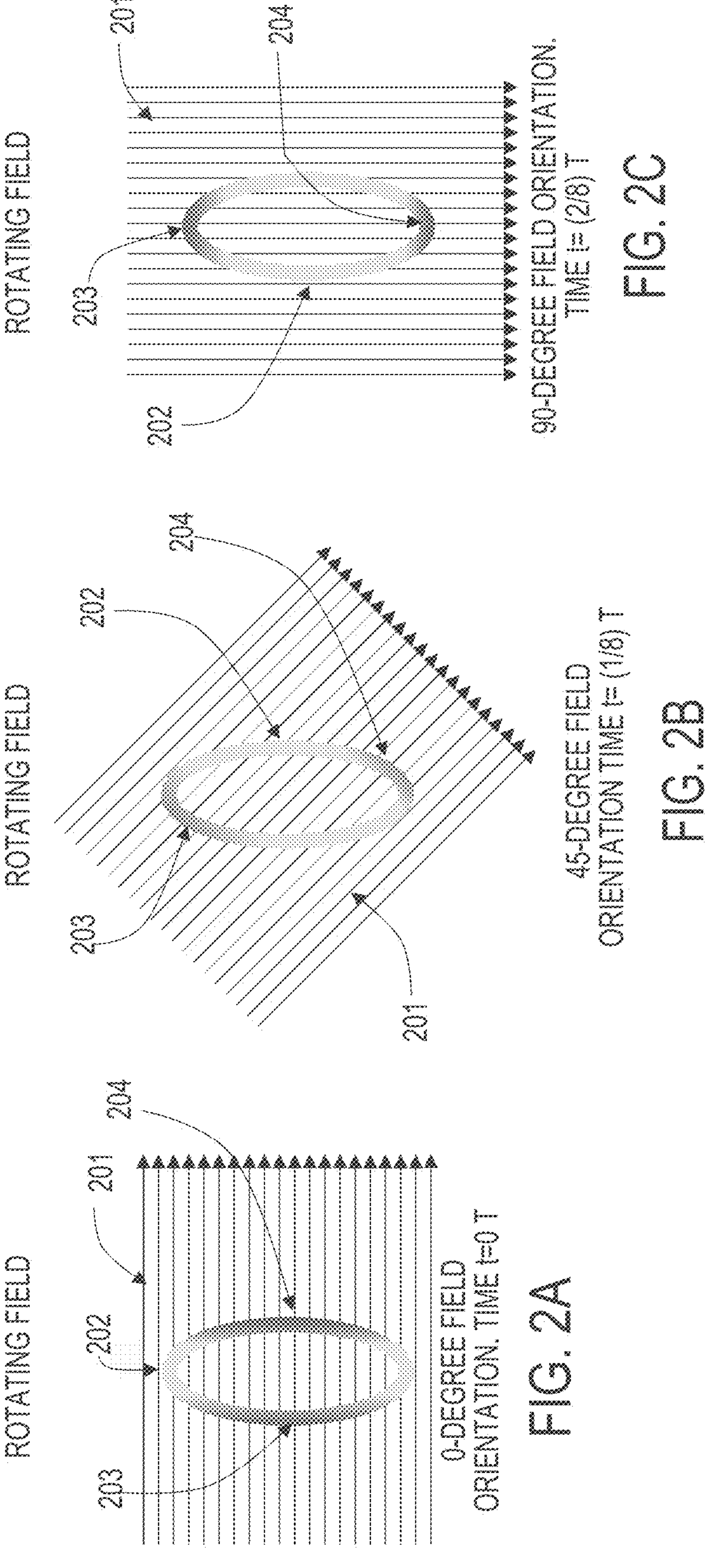
FIGS. 2A, 2B, 2C, 2D, and 2E and FIGS. 3A, 3B, 3C, and 3D together show a conceptual example of a sequence of nine time "snapshots" of an electric field, demonstrating an example of an electric field rotating in orientation.
Figure 2E:
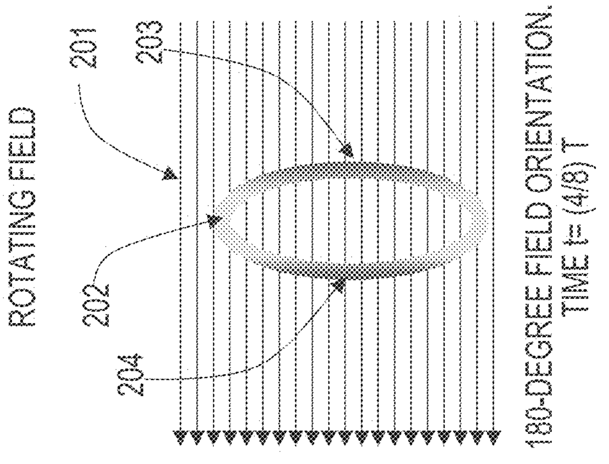
Figure 2D:
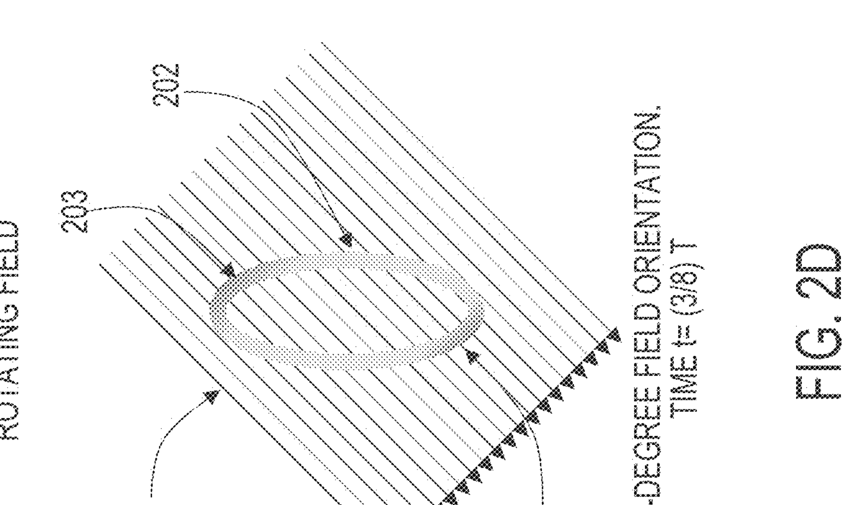
Figure 3A:
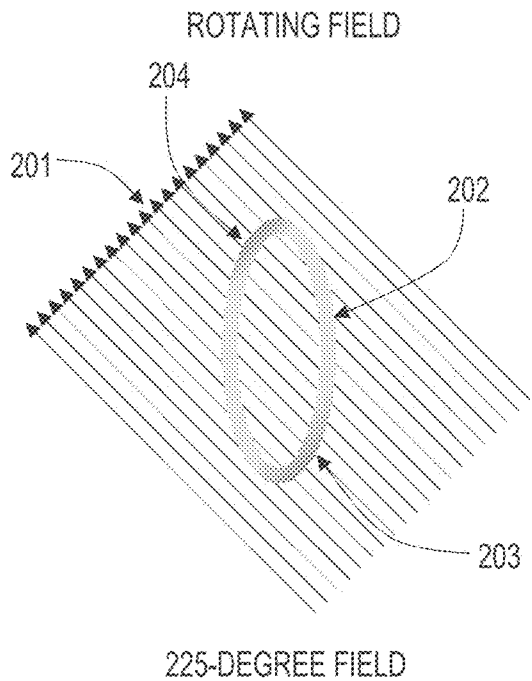
Figure 3B:
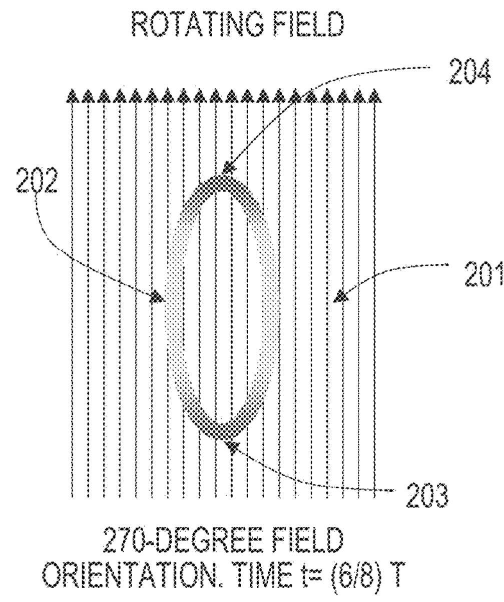
Figure 3C:
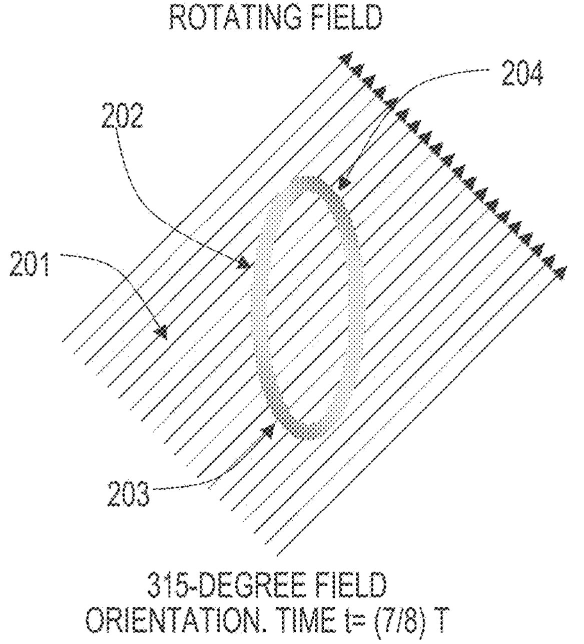
Figure 3D:
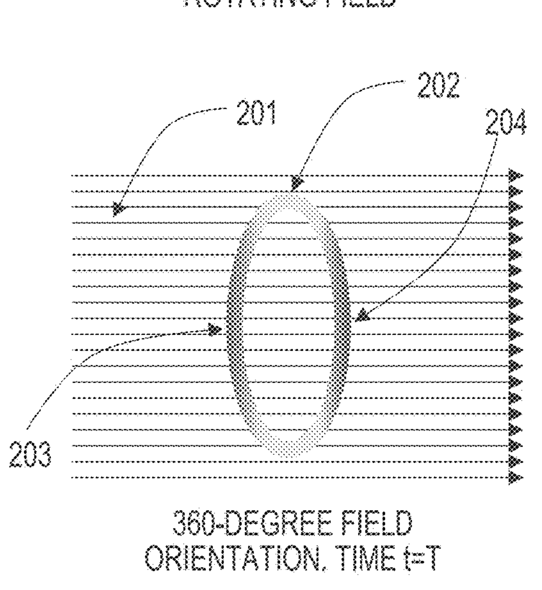

This document describes, among other things, devices, systems, methods, and other techniques of electrostimulation that can employ a rotating electric field (REF) therapy. REF therapy can employ one or more rotating electric fields, such as can be generated by a superposition or like composite of individual signal components, such as which can be provided by a triad or other set of a plurality of galvanically electrically isolated REF electrode structures. REF therapy can be employed to alter the function of biologic tissue, such as can include cardiac tissue, either on an acute or chronic basis. The present REF techniques can help reduce or minimize energy used and impact on nearby organs and tissues that are not the intended target of the REF. The REF therapy can be applied such as to be synchronized with a naturally occurring biologic function, such as to be synchronized with a cardiac ECG signal, or the REF therapy may applied such as to be asynchronous to one or more naturally occurring bioelectric signals.

For example, acute alteration of biologic tissue, such as in the case of cardiac defibrillation, can be achieved by applying an electric field level that is sufficiently high to stimulate the cardiac tissue, but below electric field levels that could cause chronic alteration or permanent damage to the cardiac tissue. However, the applied REF can be increased in energy, such as by increasing the amplitude to such a level that can achieve permanent alteration of the tissue, such where cardiac or other tissue ablation is desired, such as to alter or totally deactivate the offending tissue that was responsible for initiating cardiac arrythmias.

Certain comparative therapies for biology and medicine can include delivering energy via an electrode in galvanic contact with surrounding tissue by applying a bulk electric current. This bulk electric current flows out of one electrode, through the tissue, and into the other electrode in a pair of electrodes. In such an approach, bulk current flow is used to maintain a desired therapeutic electric field between the galvanically contacting electrodes over a duration of the applied therapy.

By contrast, the present approach can provide a system that need not rely on bulk current flow to maintain the applied electric field. Instead, the present approach can employ a rotating electric field that can be applied via electrically insulated (galvanically isolated) electrodes. Such electrically insulated (galvanically isolated) electrodes are referred to herein as "REF electrodes," which differ from conventional electrodes in that REF electrodes need not electrically galvanically contact biological tissue to deliver bulk current, but instead can capacitively couple a displacement current into the tissue. Such REF electrodes can be accessed via one or more electrically conductive wires or traces that are also overlaid with electrical insulation. Therefore, in an example, such REF electrodes can constitute the distal end portions of such conductive wires. The REF electrodes may also have a thinner overlayment of an electrical insulator than the thickness of the electrical insulator being used to access the REF electrode. This thinner electrical insulator overlaid the REF electrodes can help to promote dielectric coupling. The REF electrodes may also have a larger exposed surface area than the interconnecting wire or trace used to access the REF electrode, for similarly enhancing presentation of the electric field to the nearby (galvanically isolated) biologic tissue. Because the present REF system may also involve sensing of bioelectric cardiac signals, either intrinsic or evoked, and because such signals may involve using electrical signal sensing electrodes that are electrically in galvanic contact with biologic tissue, such sensing electrodes are not referred to herein as REF electrodes, and such sensing electrodes are not overlaid by an insulator separating such electrical signal sensing electrodes from the biological tissue.

Without being bound by theory, the REF can keep the free charge in the interelectrode tissue in motion. This can help inhibit charge from gathering at the insulated electrodes and, in so doing, cancelling the applied electric field. In addition, the REF therapy can be applied directionally from different directions toward different or even all sides of the tissue cells being targeted. Briefly, there is sometimes a preferential orientation to apply a therapeutic electric field to a cell, such as to obtain a desired effect on a cell (e.g., depolarization or interrupting a circulant arrhythmic pathway). A challenge with comparative galvanically contacting therapy modalities is that to obtain more effective applied electric field orientations, the electrodes would need to be relocated or optimally placed during an initial setup. But with a rotating electric field delivered from galvanically isolated electrodes, an entire circumference of the cells is affected by a perpendicular field as the field is rotated, e.g., through 360 degrees. This can be especially effective for tissue in which the target cells are oriented in different directions. This effect can help ensure that more of the tissue is “captured” at lower energy levels, for an intended result of the applied electrical therapy.

FIGS. 1A, 1B, and 1C are schematic diagrams that conceptually show the impact of cell geometry and electric field orientation to illustrate the interaction therebetween. The brackets indicate the areas of strongest electric field effect (e.g., for destructive therapies, e.g., ablation, this would represent the area of greatest pore formation resulting from applying the ablative therapy energy). FIG. 1A is an example of an ellipsoid cell oriented with its major axis being parallel relative to the direction of the applied electric field. FIG. 1B is an example of a circular cell, in which the larger cell area can be noted, as well as noting that the circular cell is shown as being perpendicular to the applied electric field, such as is indicated by the brackets. FIG. 1C is an example of an ellipsoid cell with its minor axis being parallel to the direction of the applied electric field. In FIG. 1C, the majority of the cell wall is shown as being exposed to the perpendicular electric field, thereby effectively increasing or maximizing the cell area that is prone to pore formation resulting from applying the ablative therapy energy.

Rather than reorienting the cell, such as is shown via FIGS. 1A, 1B, and 1C, the electric field can be rotated in space, such as via the present REF therapy. This can be accomplished by applying out of phase (e.g., differently phased) time-varying voltage signals to the insulated electrodes. The electric vectors of these time varying voltages can add to create a composite electric field that rotates, e.g., continuously, in space.

The electro-rotating electric fields that form the basis of the present REF therapy can be generated using at least three electrodes. Each electrode can be driven by a time varying signal, such as which can be shifted in time from other signals in the group. This time shift, as well as the amplitudes of the signals can be determined based on one or more factors, such as the physical distance between electrodes, the electrical impedance of tissue between the electrodes, or the like.

The number of electrodes and their spatial configuration may vary, such as to serve a specific purpose in a specific anatomy of the human (or animal) body, such as, for example, for defibrillation of a cardiac arrythmia, for cardiac ablation, for cautery or vessel sealing, among other things.

An example of a specialized implementation of this can include an annulus arrangement, such as via an annular or cylindrical electrode carrier structure (“substrate”) that can be populated across its exterior periphery with a distribution of multiple REF electrodes. For example, these electrodes can be grouped into sets of three (triads) electrodes, each of which can be employed to generate a rotating electric field. Thus, using such an arrangement, many such rotating electric fields can be concurrently generated around the exterior periphery of this annulus arrangement of electrodes. Such an annular electrode carrier structure or arrangement can be integrated with or placed at an exterior of a balloon catheter and sized to permit the arrangement to be expanded, such as into an against an ostium or other entry of a coronary or other blood vessel, such as a cardiac pulmonary vein (PV). The annular electrode carrier structure can be radially expandable, such as to be expanded to fit 360 degrees around the interior of the PV. In such a configuration, a single exposure of REF energy through the arrangement of electrode triads can expose the entire interior circumference of the PV to a desired electric field, and can thereby help achieve an overlapping REF treatment area. An electronic system can be integrated with or attached to an intravascular, subcutaneous, or other lead system that can include or be coupled to the annular or other arrangement of electrodes. The electronic system can be programmed or otherwise configured to generate and supply one or more electrical stimulation signals to deliver the therapy. The electronic system can also be programmed or otherwise configured to provide one or more desired calibration signals, such as which can be used to help determine the time shifts between the individual signals in the group of signals implementing the REF, to determine corresponding signal amplitudes, or both. The electronic system can be programmed or otherwise configured to include one or more of any desired signal-processing, control, or communication functions. For example, the electronic system may include one or more of an implantable electrical pulse generator, an external defibrillator, or a wearable defibrillator. The electronic system may include or be coupled to one or more of a catheter, lead, or the like, such as to help provide an electrical connection from an electrical signal generator of the electronic system to the electrodes and target tissue to be treated by including REF therapy. For brevity, this document focuses primarily on a subset of applications in cardiology. However, additional or alternative therapies, such as can be used with one or more other target regions, target tissues, or both, are also contemplated, such as cautery, vessel sealing, ablation, including such as which can be performed in vivo in other organs or regions.

FIGS. 2A, 2B, 2C, 2D, and 2E and FIGS. 3A, 3B, 3C, and 3D together show a conceptual example of a sequence of nine “snapshots” of an electric field 201, taken at corresponding different time instances, and demonstrating an example of the electric field 201 rotating in orientation, circularly about an imaginary central axis, through 360 degrees. The electric field 201 permeates a cell 202 as the field rotates in two-dimensional space and across time (e.g., at different times “a” through “j”). The indicated locations 203, 204 show the locations at which the respective incident and existing electric field 201 is perpendicular to a wall of the cell 202. The locations 204 show locations at which the electric field 201 is incident upon the cell wall at angles of ±45 degrees from perpendicular. The angular amount of 45 degrees was selected to define arbitrary end points to the range of the incident electric field 201, since at this range end location 204 is where the component of the electric field 201 perpendicular to the wall of the cell 202 equals the component of the electric field 201 that is tangential to the wall of the cell 202. The perpendicular component represents the portion of the applied electric field 201 that is in parallel with the natural electrical potential across the wall of the cell 202, resulting in maximal impact on the cell 202, whereas the tangential component of the electric field 201 has minimal effect on the potential of the wall of the cell 202. As illustrated, since the electric field 201 permeates the total cell 202, opposing walls of the cell 202 are exposed locally to opposite polarities of the applied electric field 201.

Without being bound by theory, rotating the electric field can expose the entirety of the wall of the cell 202 to both polarities. More particularly, the REF permeates the full cell, such that the incremental wall on one side of the cell will experience a positive polarity voltage from, e.g., the outside of the cell wall to the inside of the cell wall, whereas the incremental wall on the other side of the cell will experience a negative voltage from the outside to the inside of the cell. This is due to the incremental cell walls being “flipped” relative to the electric field. In sum, this can improve the effect on depolarizing or otherwise treating the cell, as one polarity may be more effective than another at any particular point in time or space.

Figure 4:
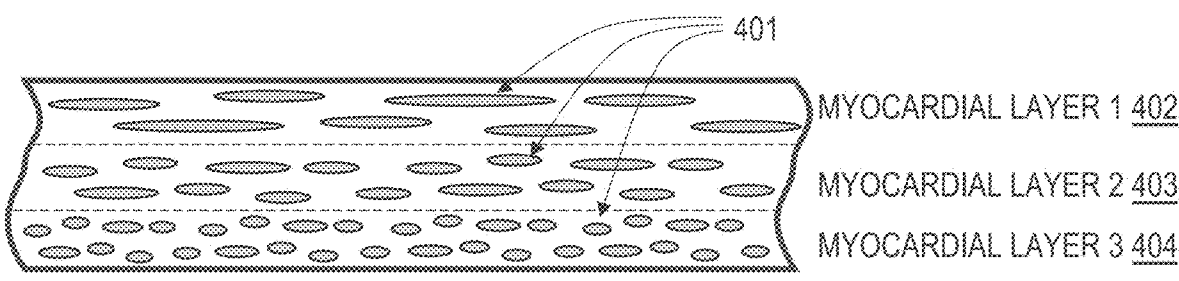
FIG. 4 and FIG. 5 are schematic illustrations that include conceptual illustrative examples showing how cells may be oriented differently throughout various layers of biologic tissue such as cardiac or other muscle.
Figure 5:
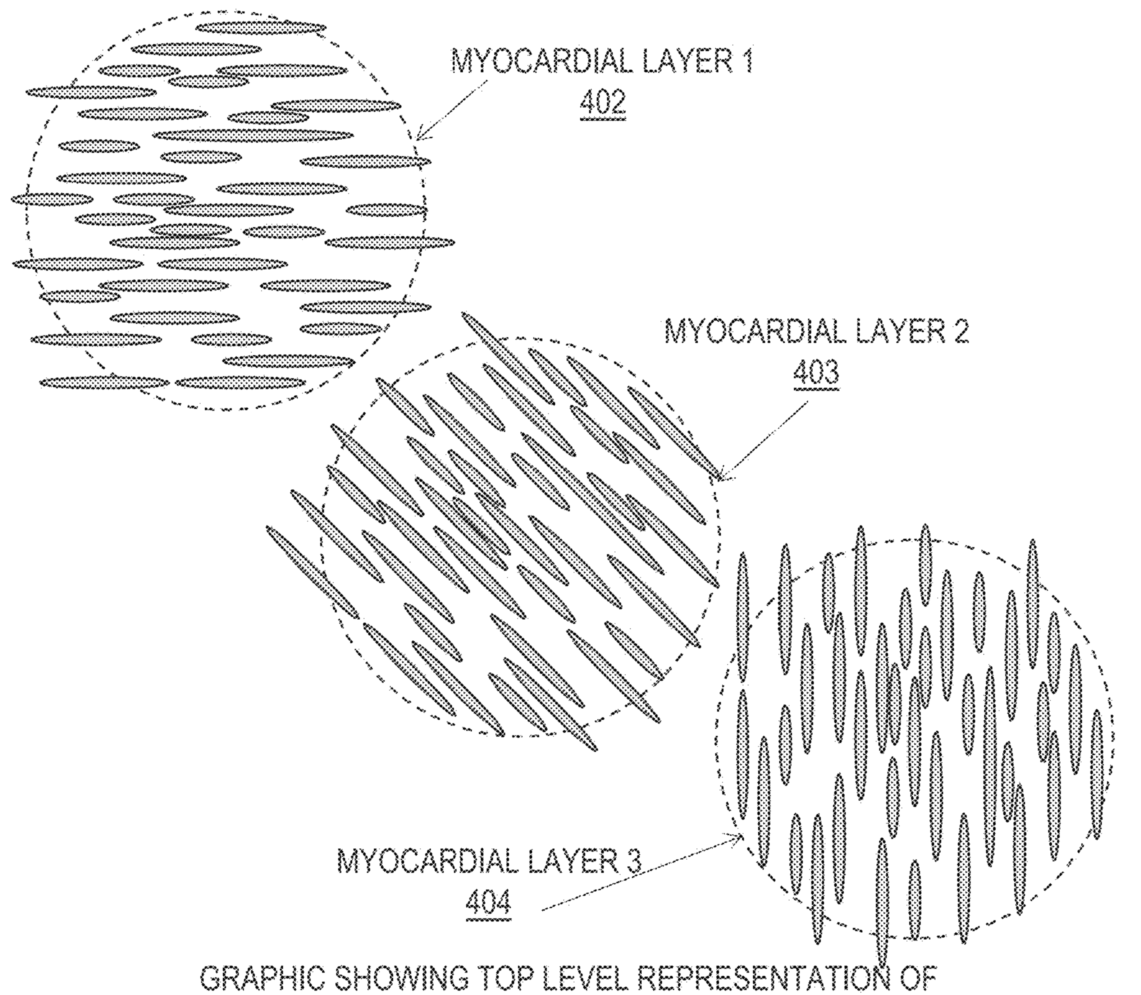

FIG. 4 and FIG. 5 are schematic illustrations that include conceptual illustrative examples showing how cells 401 may be oriented differently throughout various layers 402, 403, 404 of cardiac or other muscle. This helps further illustrate benefits of the rotation of the applied electric field 201. More particularly, the rotating nature of REF therapy can help increase the likelihood of affecting cells 401, such as by delivering energy in the form of an electric field 201 that can be rotated to be perpendicular, such as in areas defined by the locations 203, 204, to the surfaces of the cells 401. Such rotation can be in a 360-degree fashion (see, e.g., FIGS. 2 and 3) as compared to an approach employing unidirectional electric field applications, which will be perpendicular to the wall of the cells 401 over only a few degrees (see, e.g., FIGS. 1A, 1B, 1C).

Figure 6:
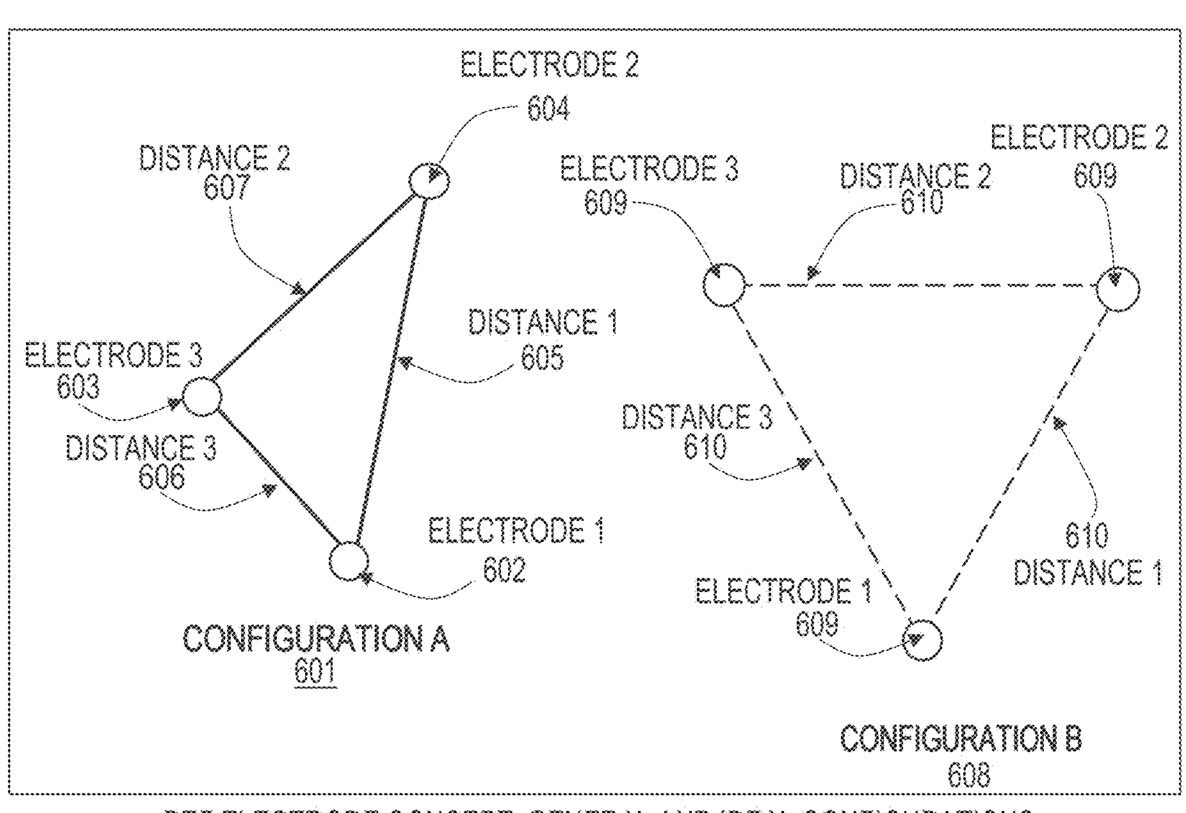
FIG. 6 is a schematic diagram that illustrates conceptual examples of a triad of three electrodes with like or different interelectrode distances.

FIG. 6 is a schematic diagram that illustrates a conceptual example of a general arrangement or configuration of a triad of three electrodes 602, 603, 604 positioned at desired arbitrary locations, such as which may be influenced by anatomy of a particular patient, such as with arbitrary interelectrode spacing (e.g., see Configuration A 601, shown at left of FIG. 6), or with an idealized equilateral triangle formed by like interelectrode spacing (e.g., see Configuration B 608, shown at right of FIG. 6). The geometry resulting from an individual one of these arrangements defines corresponding respective distances 605, 606, and 607, such as shown in FIG. 6. This type of configuration can employ applied electrical REF signals that can be identical or differ in amplitude from each other. For example, a normalization, a calibration technique can be employed to help determine or adjust one or more effective amplitude values of the respective signals being applied to the electrodes 602, 603, 604.

Figure 7:
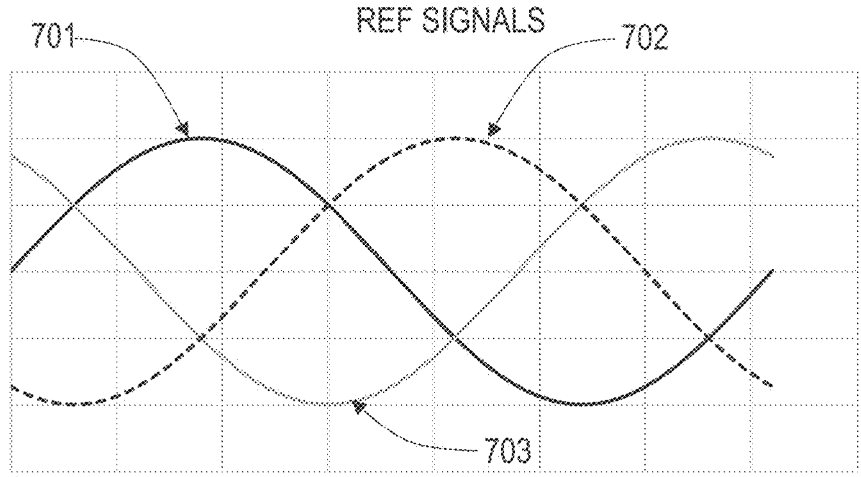
FIG. 7 is a conceptual schematic diagraph graphing amplitude vs. time for the three component REF signals that can be applied to respective electrodes in a triad to create, in combination, a composite superpositioned REF electric field.

FIG. 7 is a conceptual schematic diagram graphing amplitude vs. time for the three component electrical REF signals, such as which can be applied to respective galvanically isolated REF electrodes in a triad arrangement of such REF electrodes, such as to one or both of the triad arrangements shown in FIG. 6. Applying such component signals can create, in combination, a composite superpositioned REF electric field in a region within a boundary area defined by the REF electrodes in the triad. For example, the electrical signals shown in FIG. 7 can be applied to the equidistant triad Configuration B to produce the composite REF electric field in a region within a boundary area defined by the REF electrodes of the equidistant triad, or can be normalized, calibrated, or otherwise adjusted to be applied to the non-equidistant triad produce a similar composite REF electric field region within a boundary area defined by the non-equidistant triad, such as Configuration A.

In FIG. 7, the three REF signals 701, 702, 703, can be applied to respective REF electrodes in a triad arrangement of REF electrodes, such as to the electrode configuration B 70 of FIG. 6, with respective signals superimposed upon each other onto a single time frame to help illustrate an example of an inter-relationship of the three REF signals 701, 702, 703. In an example, the REF system can be configured such that sinusoidal REF signals 701, 702, 703, such as shown in FIG. 7, can be applied to electrodes 602, 603, 604 (Configuration A) or to electrodes 609 (Configuration B) of FIG. 6, which can be properly configured as desired, to generate a rotating electric field such as that which is represented by three examples of vectors 901A, 901B, 901C in row 2 in FIG. 9, respectively corresponding to Time A 801, Time B 805, and Time C 806.

Figure 8:
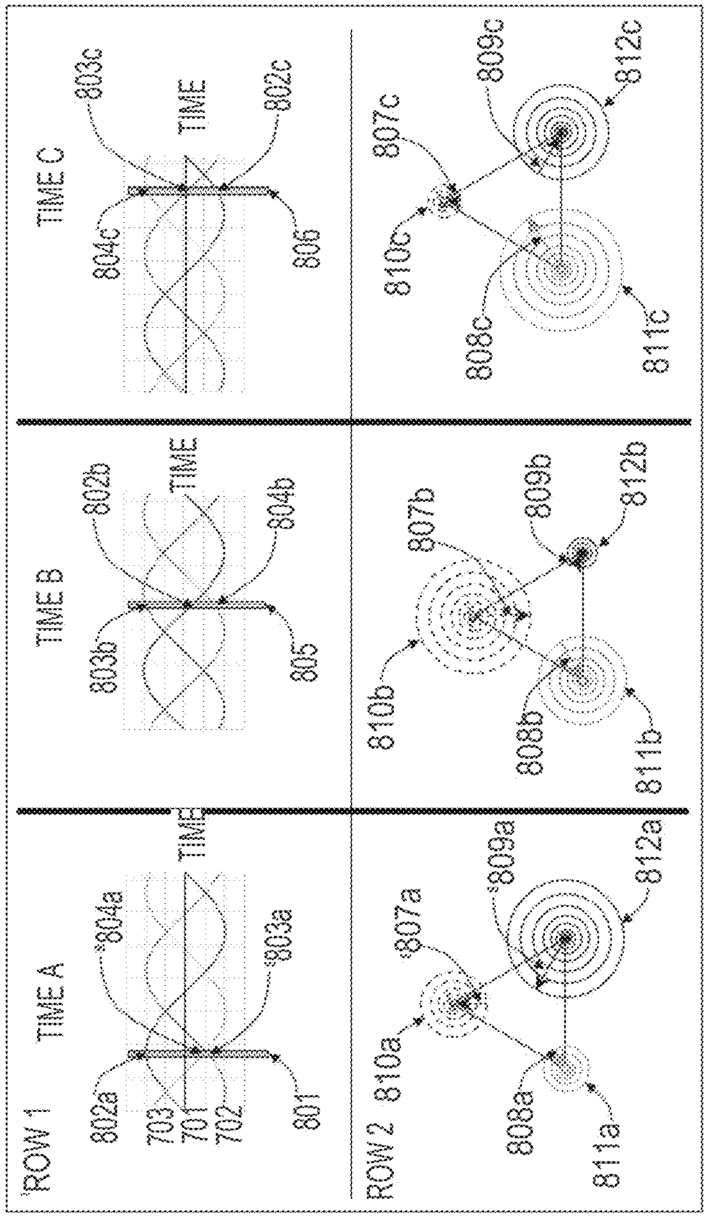
FIG. 8 shows conceptual amplitude vs. time graphs (top) of component REF signals applied to electrodes in a triad, together with resulting electric fields at the different time points (bottom).

FIG. 8 shows conceptual amplitude vs. time graphs (top) of component REF signals applied to electrodes in a triad, together with resulting electric fields at the different time points (bottom).

Figure 9:
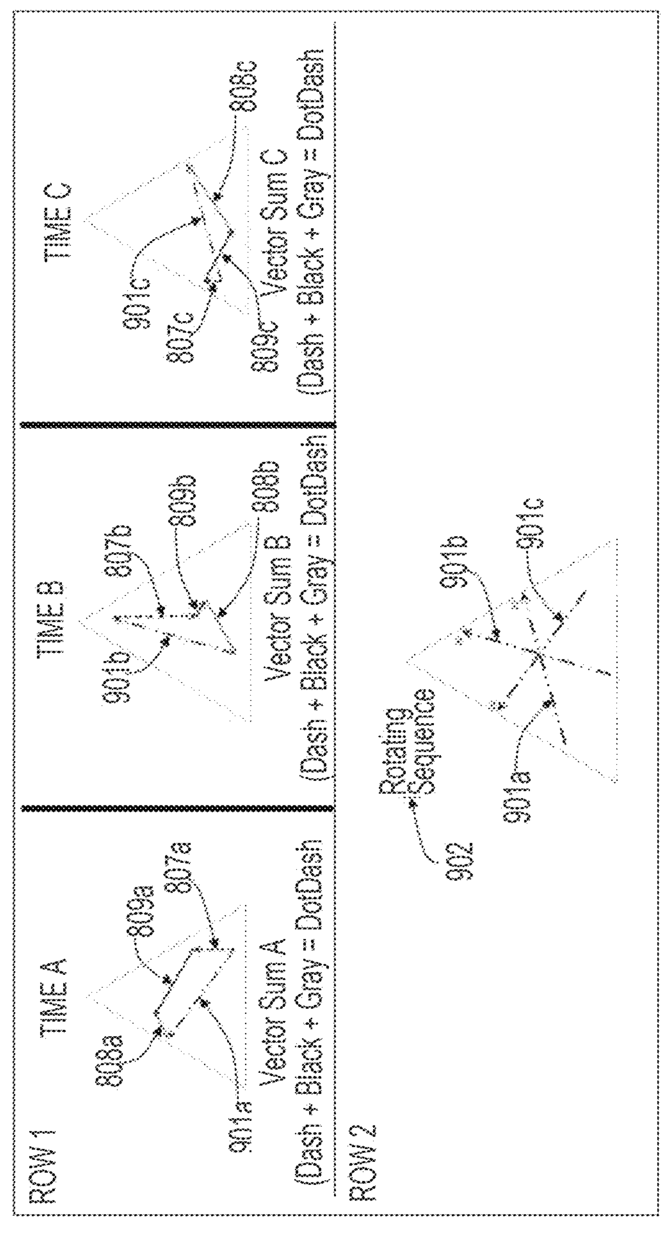
FIG. 9 shows a conceptual set of component REF field vectors at different time points (top), together with a resulting superpositioned composite REF (bottom).

FIG. 9 shows a conceptual set of component REF field vectors at different time points (top), together with a resulting superpositioned composite REF (bottom).

An illustrative conceptual example of the points in time, e.g., Time A 801, Time B 805, Time C 806 and the related parameters are captured in each column of FIG. 8 and FIG. 9, whereas each row in these FIGS. 8 and 9 provides detail related to the electric field 810A, 810B, 810C; 811A, 811B, 811C; and 812A, 812B, 812C, representative electric field vectors 807A, 807B, 807C; 808A, 808B, 808C; and 809A, 809B, 809C. A summation of vectors 901A, 901B, 901C from the electric field around each electrodes 602, 603, 604 (Configuration A) or to electrodes 609 (Configuration B) of FIG. 6 and an overall presentation 902 of the various snapshot vectors 901A, 901B, 901C occurring throughout the full rotational cycle of the summative electric field vector is shown in the bottom Row 2 of FIG. 9.

FIG. 8, row 1 is a schematic illustration that shows a full cycle of REF signals 701, 702, 703, with points in time labeled Time A 801, Time B 805, and Time C 806, which can be used to illustrate the generation of the composite rotating electric field.

FIG. 8, row 2 includes graphic schematic representations of the electric fields 810A, 810B, 810C; 811A, 811B, 811C; and 812A, 812B, and 812C as concentric circles around each of electrodes 602, 603, 604 shown in FIG. 6. These electric fields are produced by respectively applying the electrical voltage REF signals 701, 702, 703 on corresponding REF electrodes 602, 603, 604 with the corresponding sample times, e.g., Time A 801, Time B 805, and Time C 806 being selected to demonstrate an example of how the changing amplitudes over time of the voltage REF signals 701, 702, 703 can be applied so as to generate a rotating electric field.

FIG. 9 is a schematic diagram, row 1 of which shows an example of the respective electric field vectors 807A, 807B, 807C; 808A, 808B, 808C; and 809A, 809B, and 809C at corresponding electrodes 602, 603, 604 for each time sample, e.g., Time A 801, Time B 805 and Time C 806. The electric field vectors 807A, 807B, 807C; 808A, 808B, 808C; and 809A, 809B, 809C are shown as a graphic vector summation along with the corresponding single resultant vector formed by vectors 901A, 901B, 901C.

FIG. 9 at row 2 shows the three summation vectors 901A, 901B, 901C overlayed at a center of an equilateral triangle representing the area defined by the corresponding three electrodes 602, 603, 604. The resultant figure clearly shows an illustrative conceptual example of a constant amplitude vector that occurs at a different rotation point at each of the sample times.

Figure 10:
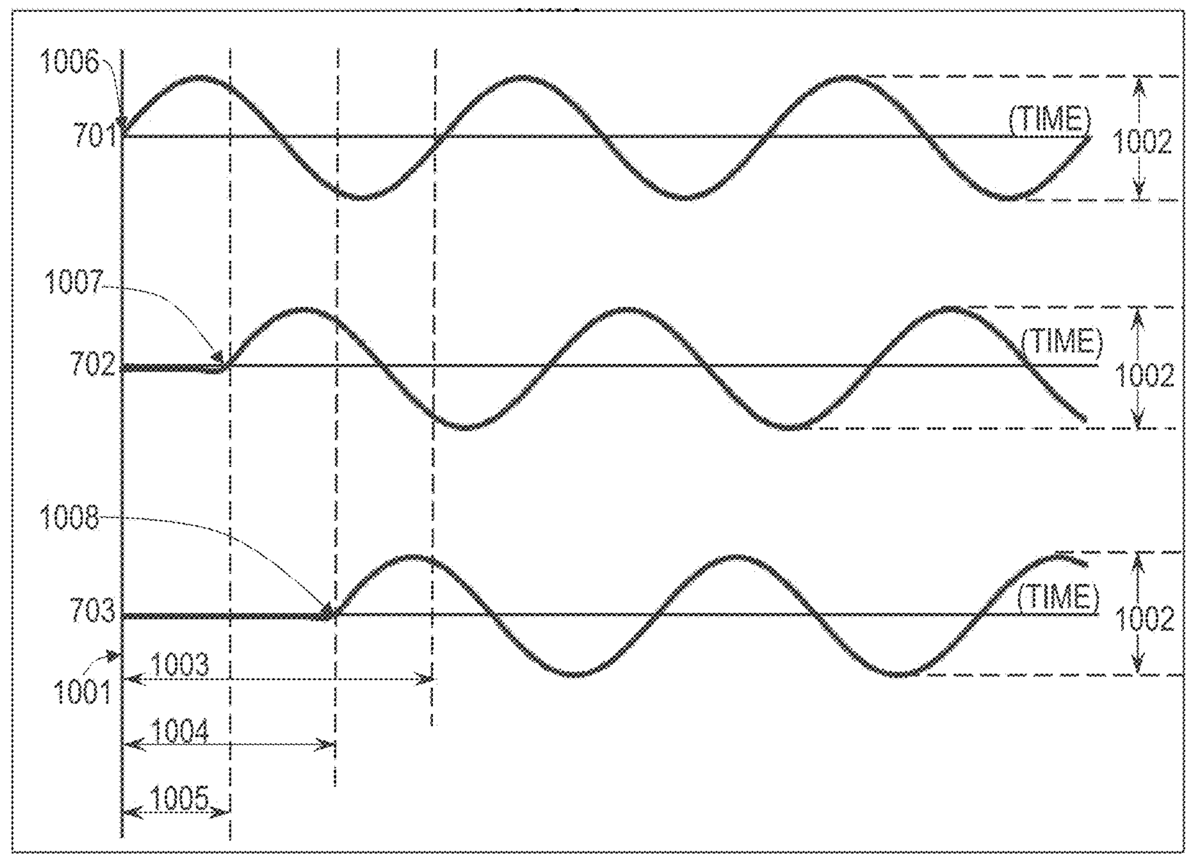
FIGS. 10-13 show phase-separated component REF electrical signals such as for applying to electrodes in a triad.

FIG. 10 is a conceptual signal amplitude vs. time graph that shows an example of the 3 REF signals 701, 702, 703 on three distinct timelines, with the timelines starting at the same point in time, to illustrate the various delays 1004, 1005 between individual ones of the three REF signals. In an example, all REF signals for the case of uniform (e.g., equidistant) electrode placements can be controllably generated to have an identical period 1003 and an identical peak signal amplitude 1002.

The start of the first REF signal 701 can occur at an arbitrary time, such as time zero 1001. The base time period 1003 of a full cycle of the first REF signal 701 can be used as the basis for the various delays 1004, 1005. The start of the second REF signal 702 can be delayed in time by a delay 1005, such as by one-third of the base period 1003. The start of the third REF signal 703 can be delayed in time by a delay 1004, such as by two-thirds of the base time period 1003.

Figure 11:
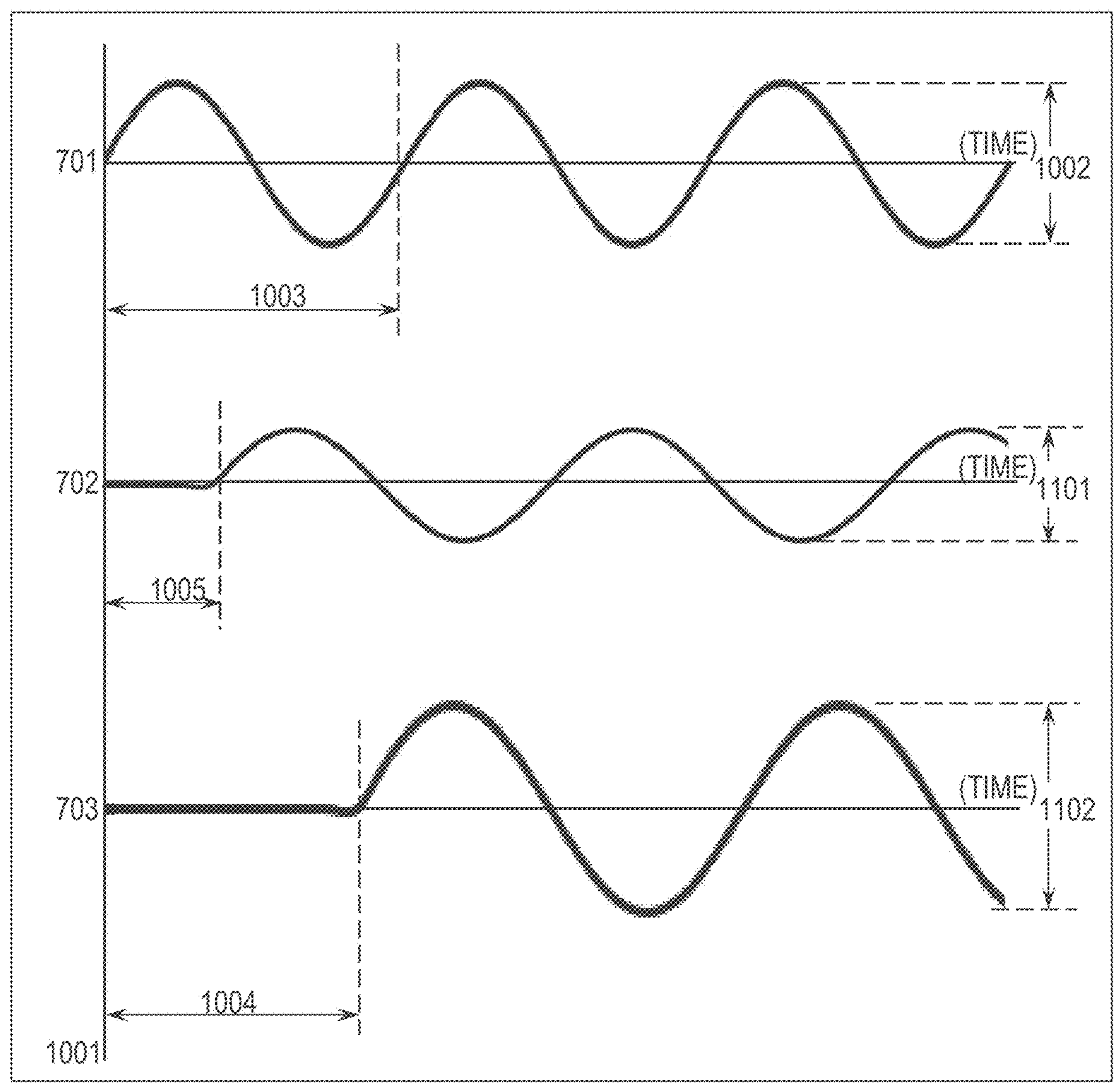
Figure 12:
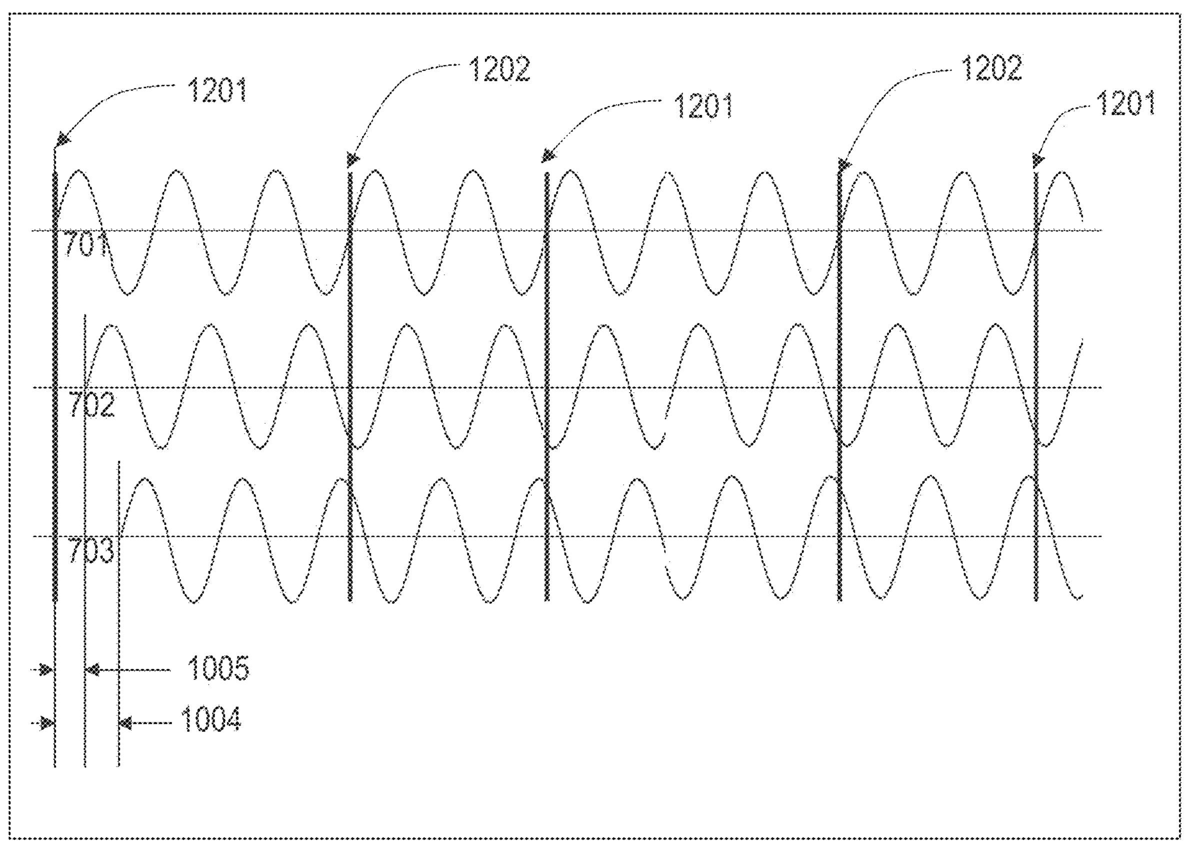

FIGS. 11-12 are schematic diagrams that shows examples of the three REF signals 701, 702, 703 on three distinct timelines, such as to help illustrate the various delays between the three REF signals for a non-symmetric REF electrode configuration as shown in FIG. 6 in association with the REF electrode Configuration A 601.

The REF signals for the case of a non-symmetric electrode configuration such as the electrodes 602, 603, and 604 as shown in FIG. 6 can have base cycle time period 1003 and corresponding maximum signal voltage amplitudes 1002, 1101, 1102, which can have values that can be based on the unique position of each REF electrode 602, 603, 604 shown in Configuration A 601 and based in the impedance of tissue between each pair of electrodes.

Figure 13:
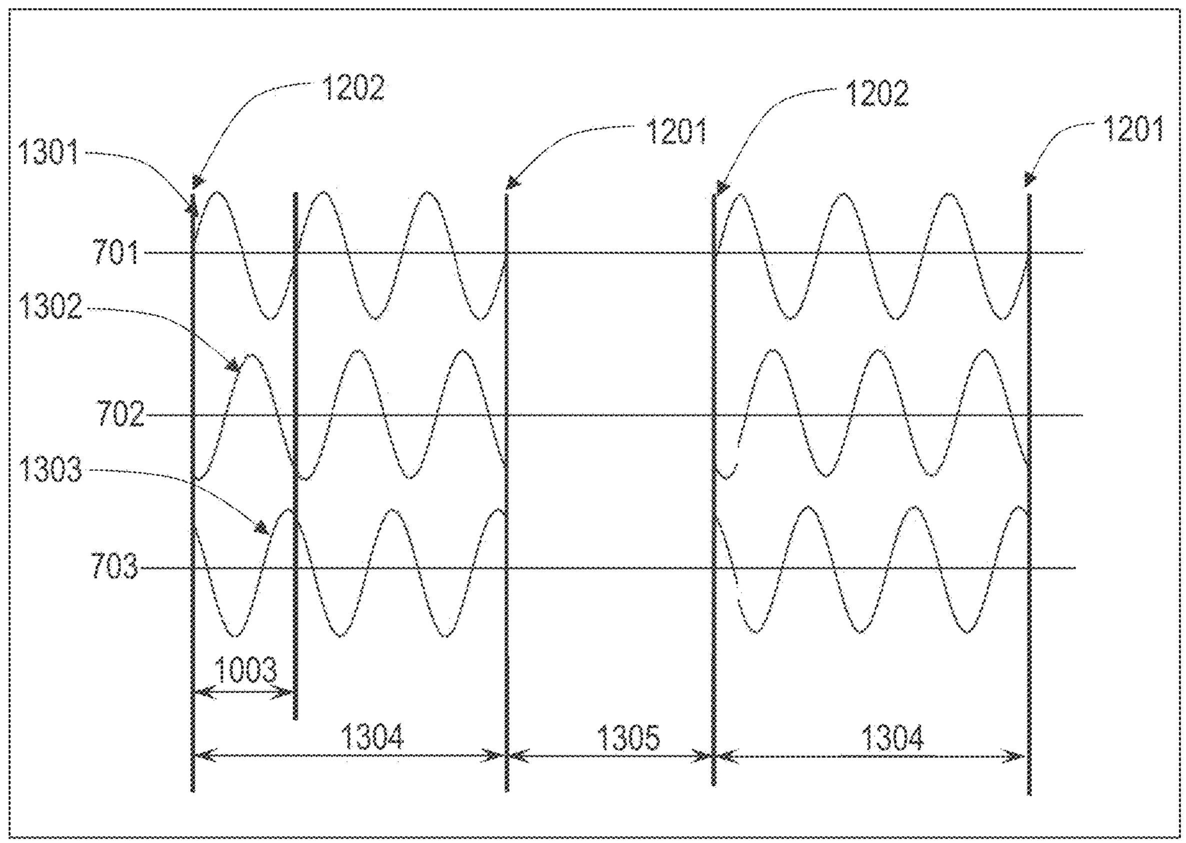

The continuous sine wave REF signals 701, 702, 703 shown in FIGS. 11-12 can be manipulated (e.g., switched, amplified, or otherwise, such as shown in FIG. 13), such as to generate an appropriate series of bursts shifted in time by phase delay 1301, 1302, 1303, interburst delays 1305, amplitude changes, or the like, such as can be controllably generated in a manner to produce a therapy signal for use in affecting the function of biologic tissue when electrodes are not positioned in a geometrically ideal fashion.

In FIG. 6, the REF electrode configuration A 601 illustrates an example of an REF electrode arrangement that can employ non-uniform positioning of the REF electrodes 602, 603, 604, such as can arise from implementation using an actual patient physiology. Further, the impedance between electrode pairs may differ significantly. To compensate for these varying characteristics, the applied voltage signal amplitudes in FIG. 11, 1002, 1101, 1102, and the base time signal period 1003 can be variable, adjustable, or both of these, such as can be based upon one or more of interelectrode distance, interelectrode impedance, or interelectrode angles such as can be defined by a triangle with the REF electrodes defining vertices of the triangle. Additionally or alternatively, the REF signals can be pulsed On/Off, such as with both the "On" duration and "Off" duration being variable, adjustable, or both. This can help allow a wide range of burst duty cycles with the number of burst cycles in a burst train as may be suitable to create effective therapeutic pulse sequences.

To signal-generate the series of REF signals, the continuous sine waves REF signals 701, 702, 703 shown in FIG. 12 can be turned on at time 1201 then turned off at time 1202, such as at specified specific points in time.

Though not a requirement for REF field generation and as shown in FIG. 13 the REF signals can be turned on at specific points in time, e.g., at time 1202 such as to begin the pulsed signal set 1301, 1302, 1303. After a predetermined time interval 1304, the signals can be turned off, such as at time 1202, such as to cease generating the first pulse of REF signals. After this generation period, a delay 1305 during which no signals are generated may be implemented before the beginning at time 1201 of generating the next set of therapy signals. Multiple pulses may not be needed, but can be available, as the system can be so configured.

The basis of REF therapy is a rotating electric field. In terms of the sine waves 1006, 1007, 1008 in FIGS. 10-12, one cycle of the sine waves, over the base time period 1003, creates one full rotation of the REF electric field. Multiple cycles of the sine waves, over multiple base time periods 1003, or multiple bursts of corresponding interval 1304 of the sine wave REF signals can be employed to create multiple corresponding rotations of the REF field.

FIG. 13 shows an example of various parameters that can be associated with the REF signal. Illustrative non-limiting examples of such parameters can include, among other things:

- Frequency (period) of sine wave 1003: 100 kHz to 500 kHz, though some implementations may lie outside this range;
- Number of sine wave cycles in a burst, the burst having an interval 1304;
- Number of bursts in treatment (occurrences of 1304); and
- Time delay 1305 between bursts.

Figure 14:
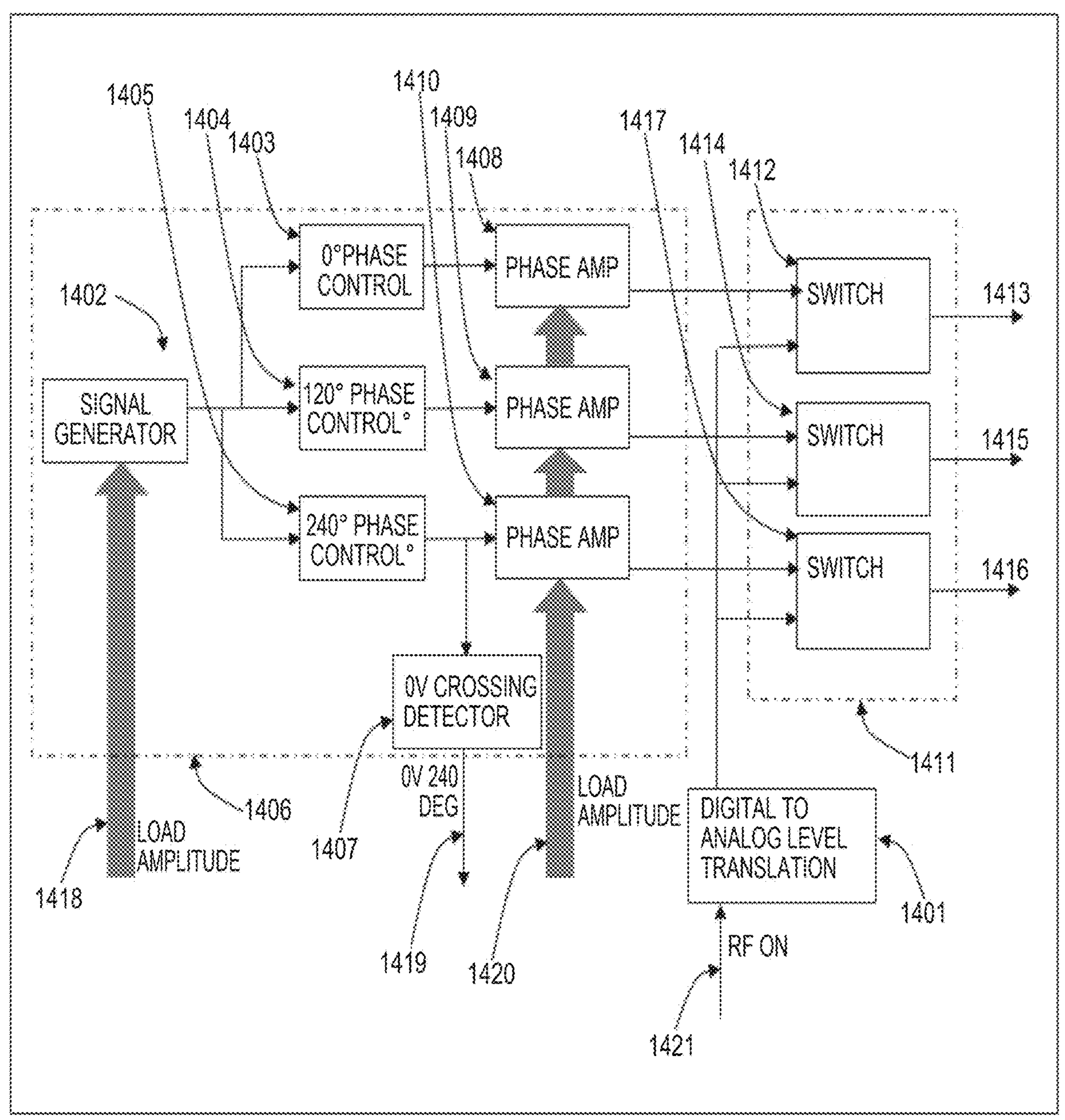
FIG. 14 shows bursts of one or more cycles of the REF signals during a therapy session, the bursts separated by a constant or variable interburst delay.
Figure 15:
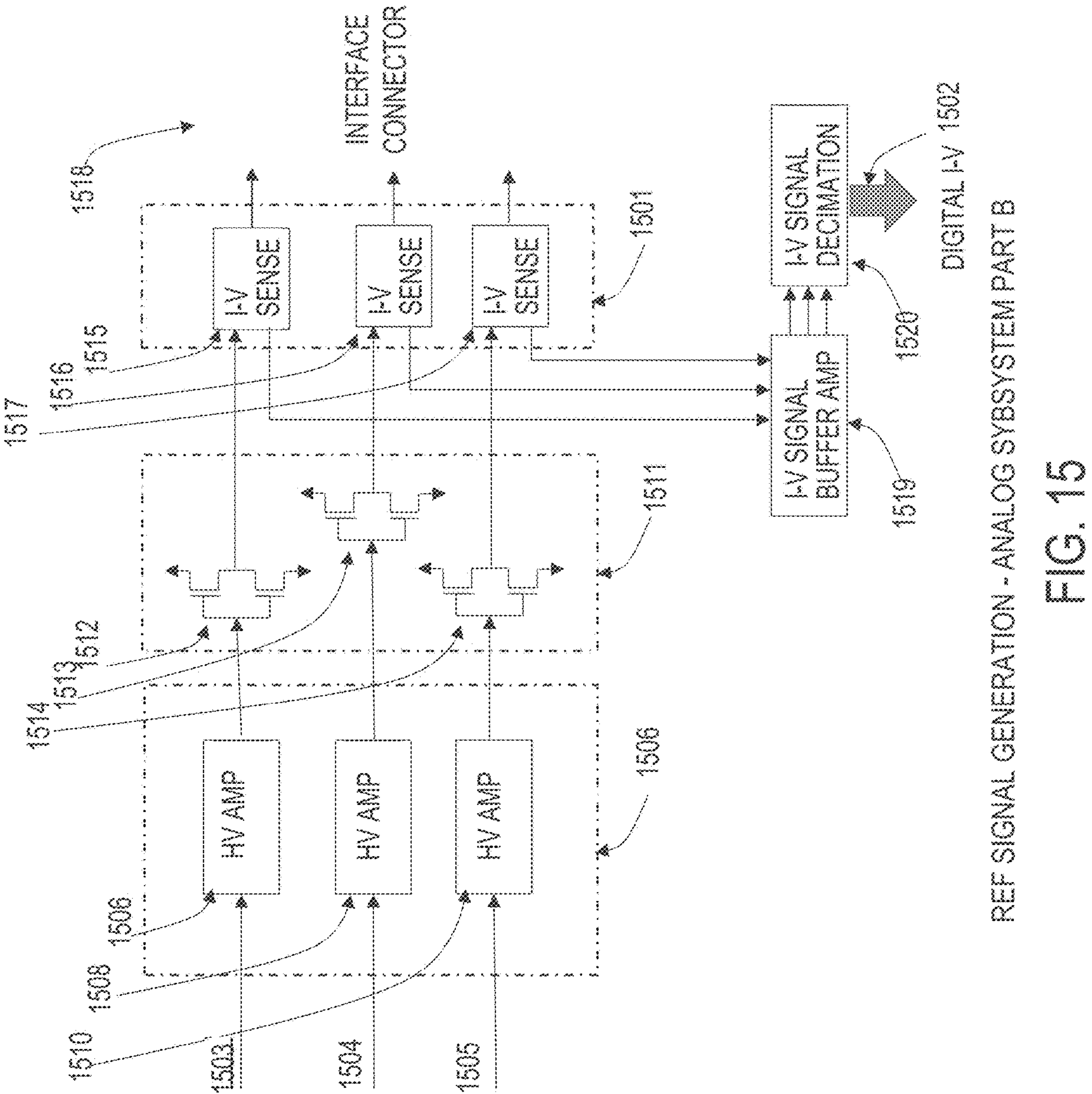
FIG. 15 is a schematic block diagram illustrating an example of portions of an analog sub-system of the present REF system.

FIG. 14 and FIG. 15 are schematic block diagrams illustrating an example of portions of an illustrative system that can include analog circuitry that can be configured to generate and supply REF signals, such as to lead or other electrodes or other devices that can be configured to interface with and deliver REF signals to biologic tissue, such as for electrostimulation or other treatment.

The circuitry can include a signal generator 1402 circuit, a switching bank 1411 circuit, amplifier 1411 circuitry, impedance matching and delivery circuitry 1511. Sensing circuitry 1501 can be configured to provide sensing of voltage, current, or both, such as delivered via the delivery circuitry 1511 during application of REF to the biologic tissue or other target.

The electrical signal generator 1402 can be configured to generate, for example, an electrical sine wave signal, e.g., either continuous-time or using a pulse-width-modulated (PWM) higher frequency "square" or similar oscillator output signal that can be low-pass-filtered into a resulting sine wave signal. The signal generator 1402 can be configured such that the frequency of this generated sine wave signal is selectable 1418, such as through a range of allowable values, such as under the control of software that can be programmed to run on a signal processor and control circuit, such as can be included at least in part in a digital subsystem, such as described with respect to FIG. 16.

The sine wave or other generated electrical signal can be routed to inputs of three phase-shift or other phase-control circuits 1403, 1404, 1405, which can respectively delay their input signals by differing amounts, e.g., 0 degrees, 120 degrees, 240 degrees. For example, the first phase-control circuit 1403 can be configured to effectively provide a zero-degree phase shift, e.g., essentially a straight-through electrical connection, with a resulting output signal that can be referred to as the "primary signal." The second phase-control circuit 1404 can be configured to provide its output signal to be delayed with respect to the primary signal, such as by 120 degrees of phase (out of a total of 360-degree period of the primary signal). The third phase-control circuit 1405 can be configured to provide its output signal to be delayed with respect to the primary signal, such as by 240 degrees of phase. The respective outputs from the phase control circuits 1403, 1404, 1405 can include a set of 3 sinusoidal "phase component" signals that can be equally spaced from each other, e.g., around a 360-degree phase diagram. Individual ones (or each) of the three respective output signals can be attenuated in amplitude by the respective phase-control circuits 1403, 1404, 1405 to a differing degree, such as can be due to differences in circuit topology.

Phase component amplifiers 1408, 1409, 1410 can include inputs respectively coupled to the outputs of the phase-control circuits 1403, 1404, 1405, such as to respectively receive their corresponding output phase component signals. The phase component amplifiers 1408, 1409, 1410 can respectively amplify their corresponding phase-component signals, such as to provide compensation or equalization. This can help compensate for differing attenuations by the phase-control circuits 1403, 1404, 1405, for example, to bring their corresponding input signals to a like amplitude, if desired. Additionally or alternatively, the phase component amplifiers 1408, 1409, 1410 can be configured to provide an adjustable amplification gain (or attenuation), such as to generate corresponding output signals that can be selected to particular amplitude values, for example, that can be selected to fall within a specified range of output amplitude values. The amplification provided by individual ones or the group of phase component amplifiers 1408, 1409, 1410 can be programmable established or adjusted, such as using an Amplitude Select procedure, such as which can be under control of system software being executed or otherwise performed by a signal processor and controller circuit, such as can be included at least in part in a digital subsystem, such as described with respect to FIG. 16.

The equalized or otherwise established or adjusted phase component signals output by the phase component amplifiers 1408, 1409, 1410 can respectively be received by the switching bank 1411 circuitry, which can include a network of corresponding switches 1412, 1414, 1417 that can be configured to control application and removal of corresponding REF therapy signals from downstream interface circuitry to electrodes associated with the biological tissue or other target.

Such downstream interface circuitry can include respective high voltage (HV) amplifiers 1507, 1510, 1508, which can respectively be configured to receive corresponding signals from the switching bank 1411 circuitry. The HV amplifiers 1507, 1510, 1508 can amplify the relatively low voltage input signals (e.g., having peak voltage signal amplitudes between X and Y, for example) to output corresponding higher voltage therapy signals, such as to provide suitable therapeutic values such as for cardioversion, defibrillation, ablation, or other desired REF therapy to be applied to the biological tissue using REFs. Such HV REF signals can be applied via the corresponding impedance matching and delivery circuitry 1511, such as via per-channel impedance matching and delivery circuitry 1512, 1513, 1514, to an interface connector 1518, which can be connected (e.g., via a catheter or other leadwire or other electrical connection) to corresponding electrodes that can be located against the biologic tissue being targeted for the particular desired REF therapy.

Figure 16:
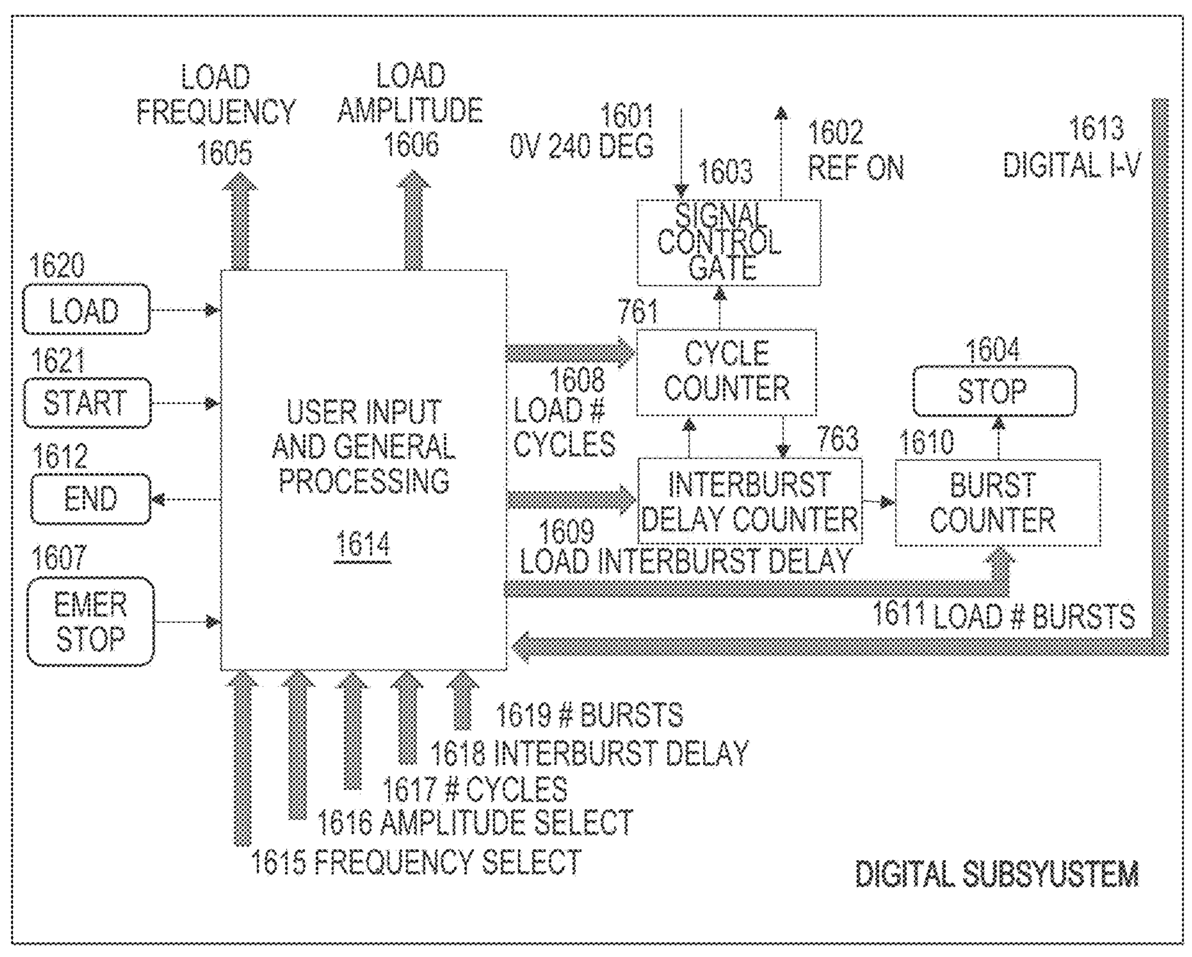
FIG. 16 is a schematic block diagram illustrating an example of portions of a digital subsystem of the present REF system.

FIG. 16 is a schematic block diagram illustrating generally portions of an example of portions of a digital circuitry subsystem, such as can be configured to interface with the analog circuitry subsystem described with respect to FIGS. 14-15, such as to provide REF therapy to biologic tissue. The digital subsystem can include a programmable signal processing and controller 1614 circuit. The controller 1614 can be programmed, for example, such as to receive a Load input 1620, a Start input 1621, an End input 1612, and an Emergency Stop input 1607, such as from a clinician or other end-user via a graphical or other user interface device or, additionally or alternatively, from a medical robot or another machine.

Other inputs that controller 1614 can be programmed to similarly receive can include, for example, a frequency selection input 1615, an amplitude selection input 1616, a number (#) of cycles 1617 (per burst) input, an interburst delay 1305 input 1618, and a number (#) of bursts 1619 per therapy session input.

The controller 1614 can be programmed to process received inputs and signals, and to provide outputs that can include, for example, a Load Frequency output 1605 and a Load Amplitude output 1606, each of which can be coupled to the signal generator 1402, such as to configure the signal generator 1402 with appropriate input parameters for a desired configuration of the signal generator 1402 for providing REF therapy control signals.

The controller 1614 can also be programmed to process received inputs and signals, to provide outputs that can include, for example, a Load Number (#) of Cycles output 1608 and a Load Interburst delay 1305 output 1609. The digital circuitry subsystem can include embedded or auxiliary digital componentry. This can include a cycle counter, such as which can be configured to count REF therapy cycles based on the Load Number (#) of Cycles output 1608. An output signal from the cycle counter can be provided as an input to a signal control gate 1603, such as which can issue of REF therapy "ON" signal 1602, such as can be synchronized with one or more phase signals at a phase input 1601 of the signal control gate 1603. Such componentry can also include an Interburst delay counter, such as which can be configured to count the interburst delay 1305 between bursts of cycle(s) of applied REF therapy. A Burst Counter 1610 can be used to count occurrences of the bursts of cycle(s) of applied REF therapy during a particular REF therapy session and, upon reaching a completion value, can issue a Stop signal 1604 such as to terminate the particular REF therapy session.

The number of sine wave cycles within the burst, which can be specified by the Number (#) of Cycles parameter input 1618, can be selected from among or varied through a range of available values, such as which can be controllably applied via the signal control gate 1603. The signal control gate 1603 can also include or use a zero crossing detector, such as to synchronize applying the signals through the RF switches 1412, 1414, 1417 to a desired phase signal.

The Cycle Counter can be configured to accept one or more inputs from the controller 1614 running embedded software, such as can define the number of sine wave cycles to be delivered in any particular burst, such as according to the Load Number (#) of Cycles output, with REF therapy being triggered by the input of a Start signal command at a Start input 1621 of the controller 1614.

Other parameters can set how many bursts should be generated (e.g., defined by the Load Burst Number (#) output 1611 within a particular therapy session and the interburst time delay (e.g., defined by the Load Interburst delay output 1609) between each REF therapy burst in the particular REF therapy session. These two parameters can be controlled by the burst counter 1610, which accepts values for the number of bursts (e.g., defined by the Load Number (#) of Bursts output 1611) in a particular REF therapy session. The interburst delay time duration between REF therapy bursts can be controlled by the Interburst Delay Counter, which accepts values for the interburst delay time interval (e.g., defined by the Load Interburst Delay output 1609) in a particular REF therapy session.

Figure 17:
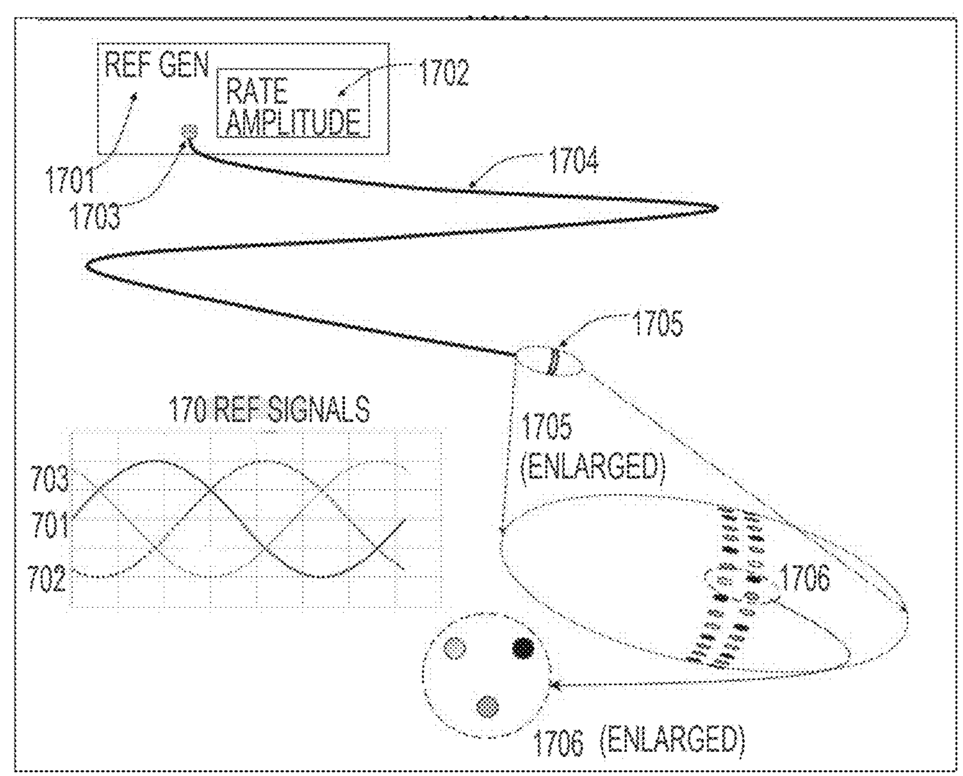
FIG. 17 is a schematic view illustrating interaction between REF system components.

FIG. 17 is a schematic diagram illustrating conceptually interaction between various components of an illustrative example implementation of a portions of a Pulmonary Vein (PV) Rotating Electric Field (REF) system. As shown in FIG. 17, an REF Signal Generator (RSG) 1701 can include a graphical or other user interface, such as which can receive a user input 1702 from an operator and, based thereupon, the RSG 1701 can generate REF signals 1707. A catheter connector 1703 on the RSG 1701 can be configured to provide the REF signals 1707 to REF electrodes in a triad 1706, such as which can be located on a balloon 1705 that can be integrated on or attached to a distal region of an REF catheter 1704. The REF catheter 1704 can include wired electrically conductive lines or connections that can respectively carry the REF signals 1707 to the REF balloon 1705, where such electrically conductive lines can respectively terminate at corresponding individual REF electrodes in a triad 1706. Imposing the REF signals 1707 on corresponding REF electrodes in a particular triad 1706 of REF electrodes cause a Rotating Electric Field that can interact with the biologic tissue, such as to alter the function of the biologic tissue. For example, atrial fibrillation (AF) tissue trigger locations or substrates can be targeted for applying the REF thereto, such as to interrupt or terminate AF or another cardiac arrhythmia in cardiac tissue.

Figure 18:
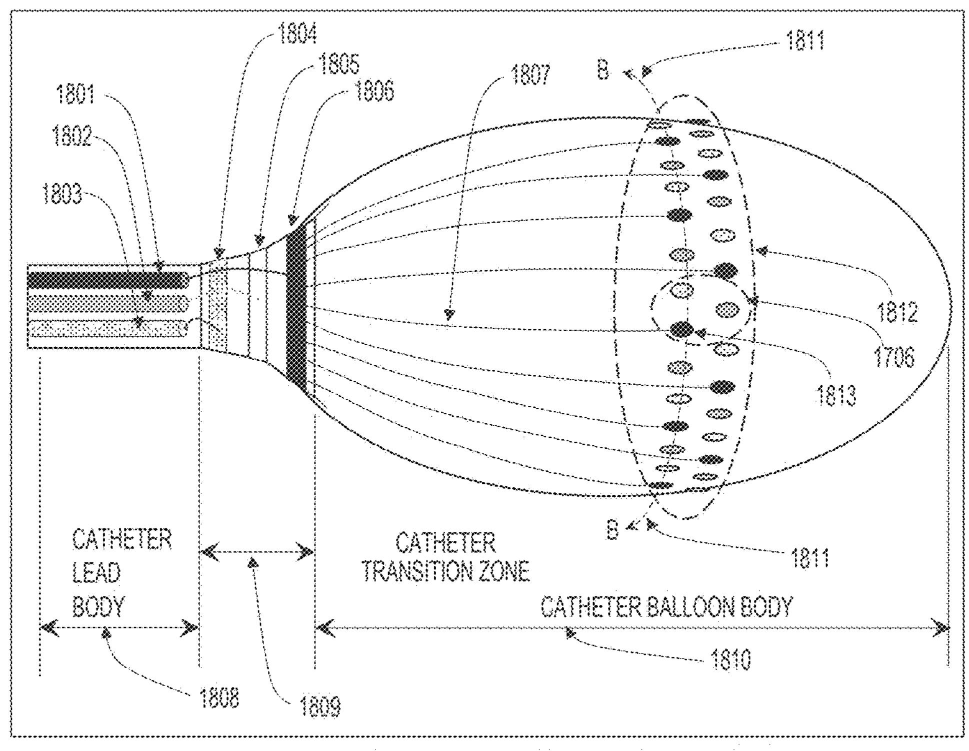
FIG. 18 is a schematic view illustrating a distal end portion of an REF catheter.

FIG. 18 is a schematic illustration that shows an illustrative example of a configuration of a distal end portion of an REF catheter 1704, such as for conveying the REF energy from the RSG 1701 to triad 1706 of REF electrodes. The lead body of the catheter 1704 can carry longitudinally extending electrically conductive lines or wires 1801, 1802, 1803, such as which can be configured and employed to respectively convey individual REF signals 701, 702, 703 of the REF signals 1707 shown in FIG. 17. At a Catheter Transition Zone 1809 to a proximal end of the balloon 1705 at a distal portion of the catheter 1704, the electrically conductive wires 1801, 1802, 1803 can be respectively connected to corresponding intermediate electrically conductive interconnect structures 1804, 1805, 1806. These intermediate interconnect structures 1804, 1805, 1806 can respectively electrically connect to the larger diameter wires 1801, 1802, 1803 to corresponding ones or sets (e.g., triads) of the finer geometry electrically conductive traces 1807 that can be printed or deposited onto or otherwise located on an expandable outer surface of the balloon 1705, which can carry the complete distal REF electrode structure 1812, which can include one or a plurality of triads or other sets of traces 1807 and triads 1706 of REF electrodes, such as can be distributed circumferentially about the balloon 1705 in an interspersed or other desired manner for applying the REF therapy as desired. The complete distal electrode structure 1812 can include triads 1706 of REF electrodes having corresponding traces 1807 electrically coupling back to the wires 1801, 1802, 1803, such as via an optional decoder/multiplexer circuitry or a wiring hub that can be included at the catheter transition zone 1809. In this way, the REF therapy from a particular REF signal 701, 702, 703 can respectively be routed to a corresponding REF electrode (or set of electrodes, e.g., in a triad 1706), such as from individual ones of the three electrically conductive (and separately insulated) catheter body wires 1801, 1802, 1803 intended to deliver that particular corresponding REF signal 701, 702, 703.

Figure 19:
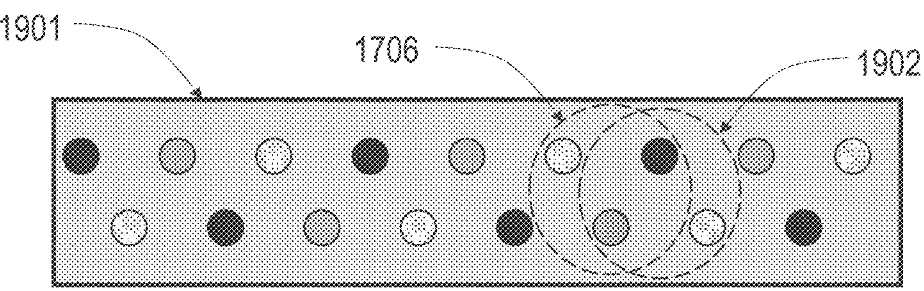
FIG. 19 is a schematic view illustrating an example of how groups of triads of electrodes can be located about a circumferential periphery of a substrate device.

FIG. 19 is a schematic view illustrating an example of how groups of triads 1706, 1902 of REF electrodes can be distributed, positioned, or otherwise located, such as about a circumferential periphery of the balloon 1705, such as to deploy the triads 1706, 1902 of REF electrodes to be used as individual triads 1706, 1902 or as concurrently employed interspersed or other groups of triads 1706, 1902 of REF electrodes to create a long flat or curved surface rectangular REF therapy application zone 1901, such as about all or a portion of surface about the circumferential periphery of the balloon 1705. As illustrated in FIG. 19, triads 1706, 1902 of REF electrodes are examples of how a plurality of triads 1706, 1902 of REF electrodes can be located with respect to each other such that each triad 1706, 1902 of REF electrodes can be employed to provide a corresponding local REF field. By configuring multiple triads 1706, 1902 of REF electrodes respectively overlapping adjacent triads 1706, 1902 of REF electrodes, individual ones of the REF electrodes in the triads 1706, 1902 can be shared during application of REF therapy, such as in a manner that can jointly create the long rectangular REF therapy application zone 1901. This, in turn, can employ the applied REF therapy in a manner that can help provide a rectangular lesion (e.g., if that is the desired therapeutic result) consistent with a desired morphology.

Figure 20:
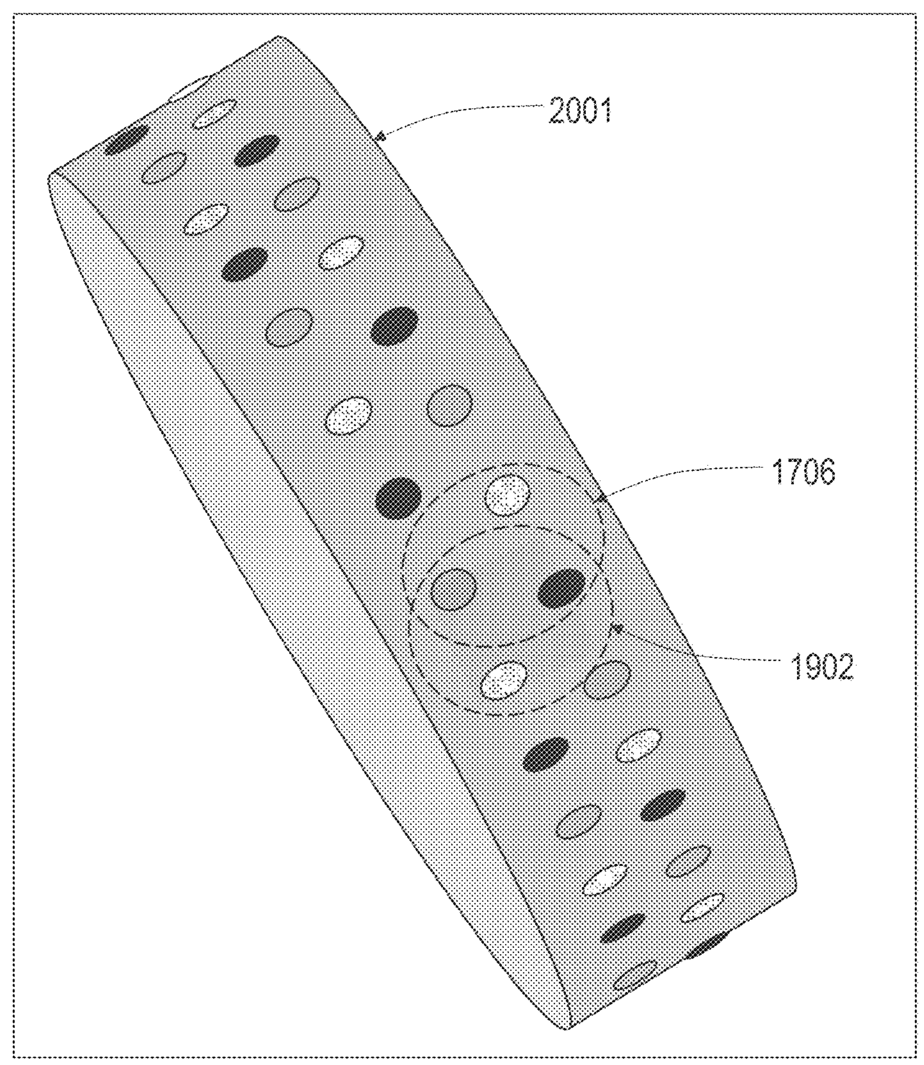
FIG. 20 is a schematic view illustrating an example of how groups of triads of electrodes can be located annularly about a periphery of a substrate device.

FIG. 20 is a schematic view, similar to FIG. 19, but showing an arrangement in which groups of triads 1706, 1902 of REF electrodes can be distributed, positioned, or otherwise located, such as arranged in an annular ring 2001 extending about a circumferential periphery of the balloon 1705, such as to deploy the triads 1706, 1902 of REF electrodes to be used as individual triads 1706, 1902 or as concurrently employed with interspersed or other groups of triads 1706, 1902 of REF electrodes to create a long curved annular surface rectangular REF therapy application zone 1901, such as can extend completely around a circumferential periphery of the balloon 1705. This, in turn, can employ the applied REF therapy in a manner that can help provide an annular lesion (e.g., if that is the desired therapeutic result) consistent with a desired morphology.

Figure 21:
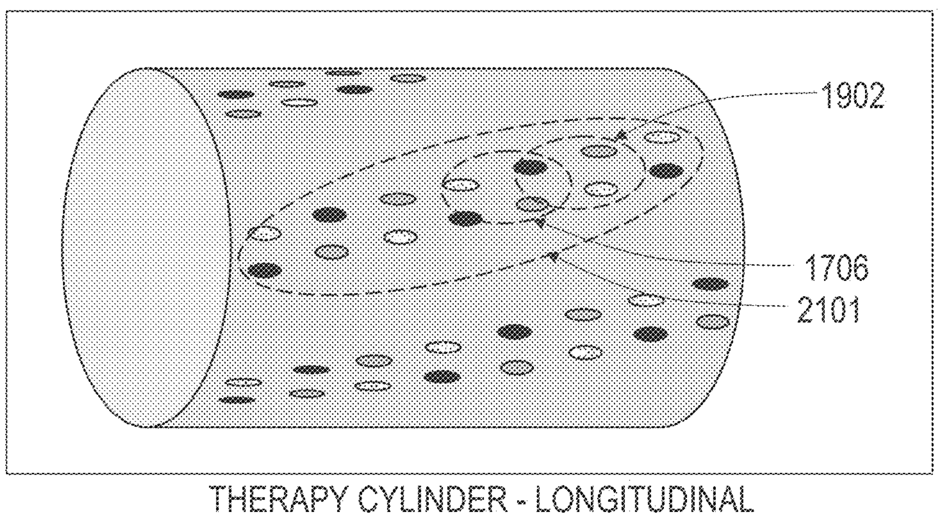
FIG. 21 is a schematic view illustrating an example of how groups of triads of electrodes can be located longitudinally (straight or helical) on a substrate device.

FIG. 21 is a schematic view, similar to FIGS. 19-20, but showing an arrangement in which groups of triads 1706, 1902 of REF electrodes can be distributed, positioned, or otherwise located, such as in one or more longitudinal strip REF application areas 2101 extending linearly or winding helically in a longitudinal direction, such as on the surface of a balloon 1705 or catheter or other elongate structure. The straight linear or wound helical strip REF application areas 2101 of triads 1706, 1902 of REF electrodes can extend longitudinally about such as about a corresponding desired base structure, such as to deploy the triads 1706, 1902 of REF electrodes to be used as individual triads 1706, 1902 or as concurrently employed with interspersed or other groups of triads 1706, 1902 of REF electrodes to create one or more corresponding REF therapy application areas 2201. This, in turn, can employ the applied REF therapy in a manner that can help provide a straight linear longitudinal or helical longitudinal lesion (e.g., if that is the desired therapeutic result) consistent with a desired morphology. In FIG. 21, the helical longitudinal REF strip application areas 2101 can be configured to keep the equilateral structure of the electrodes in the individual triads 1706, 1902 of REF electrodes intact, thereby allowing applying REF signals of consistent and equal amplitude and phasing. A correspondingly shaped lesion can be created from such a structure, such as can be intended to help break the circulant or other arrhythmogenic paths in the biological tissue, such as to help inhibit or prevent AF or other arrhythmias from initiating or persisting in the biological tissue about the PV or other desired location.

Figure 22:
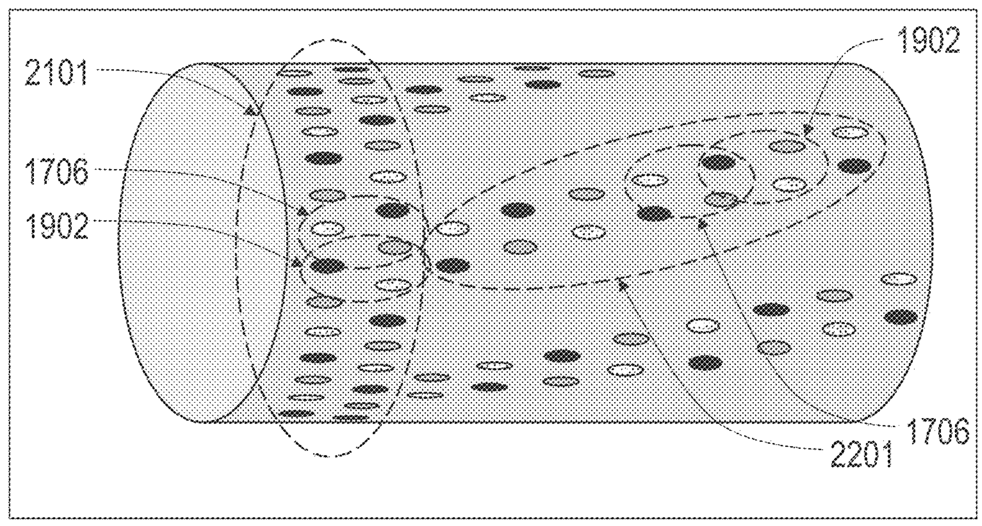
FIG. 22 is a schematic view illustrating an example of how groups of triads of electrodes can be located annularly and longitudinally (straight or helical) on a substrate device.

FIG. 22 is a schematic view, similar to FIGS. 19-21, but showing an arrangement in which groups of triads 1706, 1902 of REF electrodes can be distributed, positioned, or otherwise located, both in an annular ring REF application area 2101 and also in one or more REF application longitudinal strips REF application areas 2201 extending linearly or winding helically in a longitudinal direction, such as on the surface of a balloon 1705 or catheter or other elongate structure. In using an arrangement such as shown in FIG. 22, after the balloon 1705 has been inserted into an ostia of a PV or other structure, an annular lesion can be created by applying REF therapy to the groups of triads 1706, 1902 of REF electrodes forming the annular ring 2001, and linear or helical longitudinal lesions can be additionally or alternatively created by applying the REF therapy to the groups of triads 1706, 1902 of REF electrodes forming the straight linear or helical longitudinal strip REF application areas 2201. This combination of an annular REF application area 2101 and one or more longitudinal strip REF application areas 2201 can be employed such as to create corresponding lesions in adjacent biological tissue that can help minimize arrhythmogenic tendencies of such tissue and can also help block any remaining arrhythmias from progressing into the atria.

Figure 23:
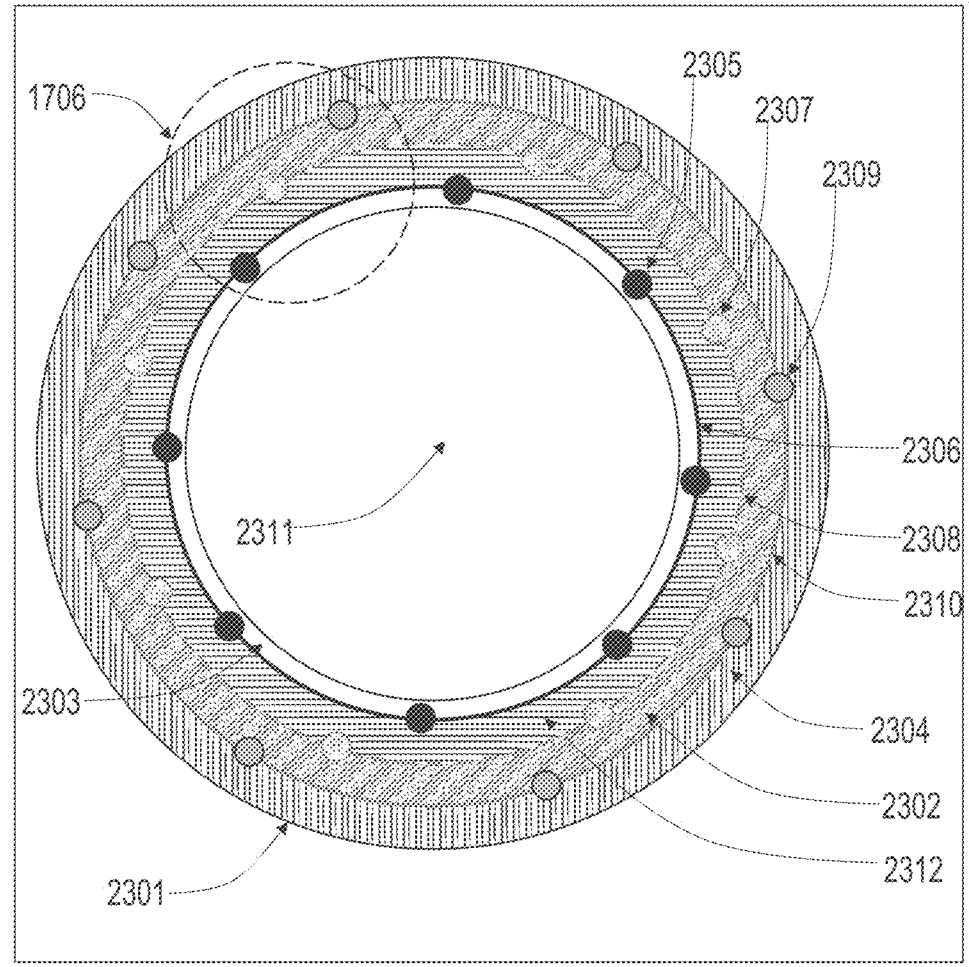
FIG. 23 is a cross-sectional view, taken at BB of FIG. 18, perpendicular to a longitudinal central axis of the balloon or other substrate device.

FIG. 23 is a cross sectional view, taken at BB 1811 of FIG. 18, perpendicular to a longitudinal central axis of the balloon 1705. In FIG. 23, an expandable electrically insulating inner-most first layer 2303 of an expandable balloon 1705 structure can include a laterally outward face that can carry a first set of electrically conductive REF electrodes 2305 (and corresponding electrically conductive traces 1807 for being routed back to a corresponding individual one of wires 1801, 1802, 1803). The first set of electrically conductive REF electrodes 2305 can be configured to serve as corresponding first triad elements in one or more triads 1706, 1902 of REF electrodes for applying REF therapy to biologic tissue, such as when the balloon 1705 is in an expanded configuration.

Proceeding laterally outward in FIG. 23, an expandable electrically insulating second layer 2311 of the expandable balloon 1705 structure can be formed on the first layer 2303 (and upon the REF electrodes 2305 and their corresponding traces 1807). The second layer can include embedded therein a second set of electrically conductive REF electrodes 2307 (and corresponding electrically conductive traces 1807 for being routed back to a corresponding individual one of wires 1801, 1802, 1803). The second set of electrically conductive REF electrodes 2307 can be configured to serve as corresponding second triad elements in one or more triads 1706, 1902 of REF electrodes, for applying REF therapy to biologic tissue, such as when the balloon 1705 is in an expanded configuration. An outer face of the second layer can carry a third set of electrically conductive electrodes 2309 (and corresponding electrically conductive traces 1807 for being routed back to a corresponding individual one of wires 1801, 1802, 1803). The third set of electrically conductive REF electrodes 2309 can be configured to serve as corresponding third triad elements in one or more triads 1706, 1902 of REF electrodes, for applying REF therapy to biologic tissue, such as when the balloon 1705 is in an expanded configuration.

Proceeding further laterally outward in FIG. 23, an expandable electrically insulating third layer 2311 of the expandable balloon 1705 structure can be formed on the first layer 2303 (and upon the REF electrodes 2305 and their corresponding traces 1807). The second layer can include embedded therein a second set of electrically conductive REF electrodes 2307 (and corresponding electrically conductive traces 1807 for being routed back to a corresponding individual one of wires 1801, 1802, 1803). The second set of electrically conductive REF electrodes 2307 can be configured to serve as corresponding second triad elements in one or more triads 1706, 1902 of REF electrodes for applying REF therapy to biologic tissue, such as when the balloon 1705 is in an expanded configuration. The third set of electrically conductive REF electrodes 2309 can be configured to serve as corresponding second triad elements in one or more triads 1706, 1902 of REF electrodes for applying REF therapy to biologic tissue, such as when the balloon 1705 is in an expanded configuration. The outermost expandable electrically insulating layer 2304 can serve as an outer insulator that can separate laterally inward electrically conductive layers, such as including electrodes and traces, from the biologic fluids and tissues. The air or other fluid inflation chamber of the balloon 1705 is depicted at 2311. Because the REF electrodes 2305, 2307, 2309 are separated from the biologic tissue by one or more electrical insulators, such REF electrodes 2305, 2307, 2309 are not required to directly contact biologic tissue. Thus, the REF therapy being applied by individual ones of the REF electrodes in a triad 1706, 1902, 2305, 2307, 2309 can create an REF electric field that can be applied to the biologic tissue across an electrically insulating dielectric-such that no electrical conduction current of charge carriers across the dielectric barrier need be employed. Instead, the REF therapy can be reactively (e.g., capacitively) applied via a displacement current.

Figure 24:
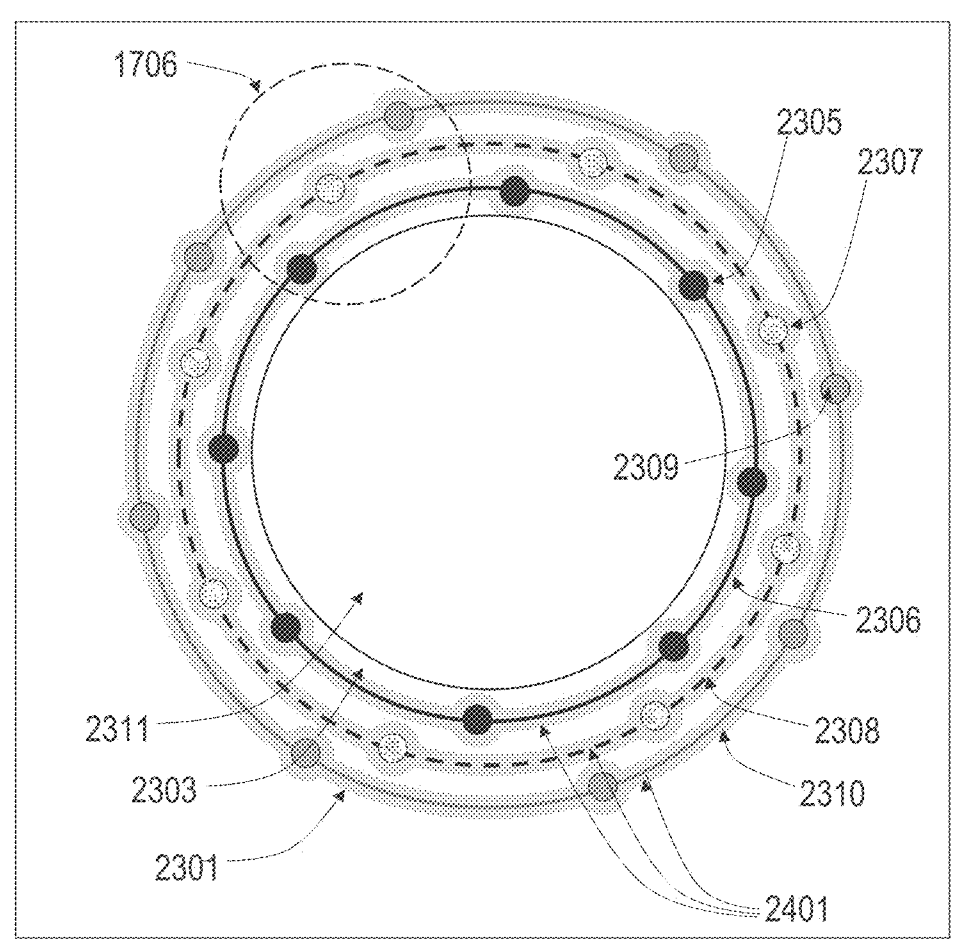
FIG. 24 is a cross-sectional view, similar to that of FIG. 23, shows an example of a different arrangement.

FIG. 24 is a cross sectional view, similar to that of FIG. 23, taken at BB 1811 of FIG. 18, perpendicular to a longitudinal central axis of the balloon 1705. FIG. 24 shows an example of a different arrangement or method of construction of the various layers of the balloon 1705 than what is shown in FIG. 23. In the example of FIG. 24, the various layers can include additional layers that can be formed upon an available balloon 1705. In FIG. 24, the balloon wall first layer 2303 is depicted as the inner-most layer in the arrangement shown. First, second, and third layers of a corresponding set of first REF electrodes 2305, a corresponding set of second REF electrodes 2307, and a corresponding set of third REF electrodes 2309 can be formed in corresponding layers on the inner-most balloon wall first layer 2303, separated from each other by corresponding electrically insulating layers. In this example, an electrically insulating coating formed upon the outer electrodes 2309 and their corresponding electrical traces 1807 can act to dielectrically separate and galvanically isolate these electrically conductive components from the surrounding biologic fluids and tissues.

Figure 25:
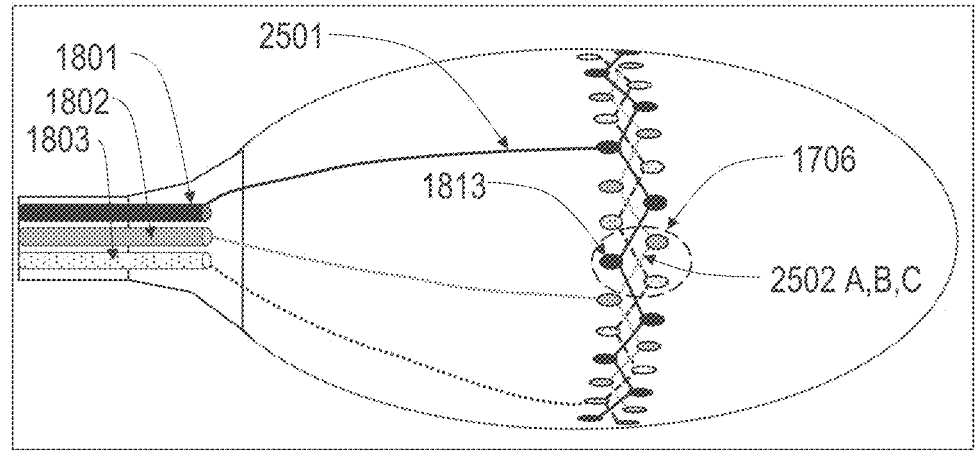
FIG. 25 is a schematic illustration, similar to FIG. 18, that shows an illustrative example of a configuration of a distal end portion of an REF catheter.

FIG. 25 is a schematic illustration, similar to FIG. 18, that shows an illustrative example of a configuration of a distal end portion of an REF catheter 1704, such as for conveying the REF energy from the RSG 1701 to the REF electrodes in a triad 1706. FIG. 18 depicted an example in which individual electrically conductive REF electrodes in the triads 1706 were accompanied by individual electrically conductive traces 1807 individually extending proximally toward connecting rings or other shared electrically conductive structures located toward a proximal end of the balloon 1705, FIG. 25 shows an alternative (or additional) structure for more locally electrically connecting corresponding REF electrodes in a triad 1706, 1902 for receiving a desired one of the three signals being delivered to a desired one of the REF electrodes in a triad 1706, 1902 in the one or more triads 1706, 1902 of REF electrodes. Because the different triad members of REF electrodes 2305, 2307, 2309 are arranged to be on different layers with other like triad members (e.g., one of REF electrodes 2305, 2307, 2309) that are intended to receive a shared selected one of the REF signals 701, 702, 703 for applying a particular phase of the REF therapy along with other like triad members, they can be locally interconnected by electrically conductive electrical traces that need not individually extend back proximally toward a proximal end of the balloon 1705, such as shown in FIG. 25. For example, FIG. 25 shows a zig-zag pattern of three electrically conductive traces 2502A, 2502B, 2502C, each of which can run circumferentially about the balloon 1705. The respective serpentine or zig-zag patterns of the three electrically conductive traces 2502A, 2502B, 2502C can leave an unobstructed path for exposing the various electrodes toward the biological tissue circumferentially surrounding the expanded balloon 1705. In an example, the surface area of the REF electrodes 2305, 2307, 2309 can be larger than the surface area of the interconnecting electrically conductive traces 2502A, 2502B, 2502C, so that the capacitive coupling provided by the REF electrodes 2305, 2307, 2309 dominates over any capacitive coupling provided by the interconnecting electrically conductive traces 2502A, 2502B, 2502C carrying respective signals to their respective REF electrodes 2305, 2307, 2309. The individual ones of the local interconnecting electrically conductive traces 2502A, 2502B, 2502C can be respectively coupled to the wires 1801, 1802, 1803, by corresponding proximally longitudinally extending electrically conductive traces 2501.

Figure 26:
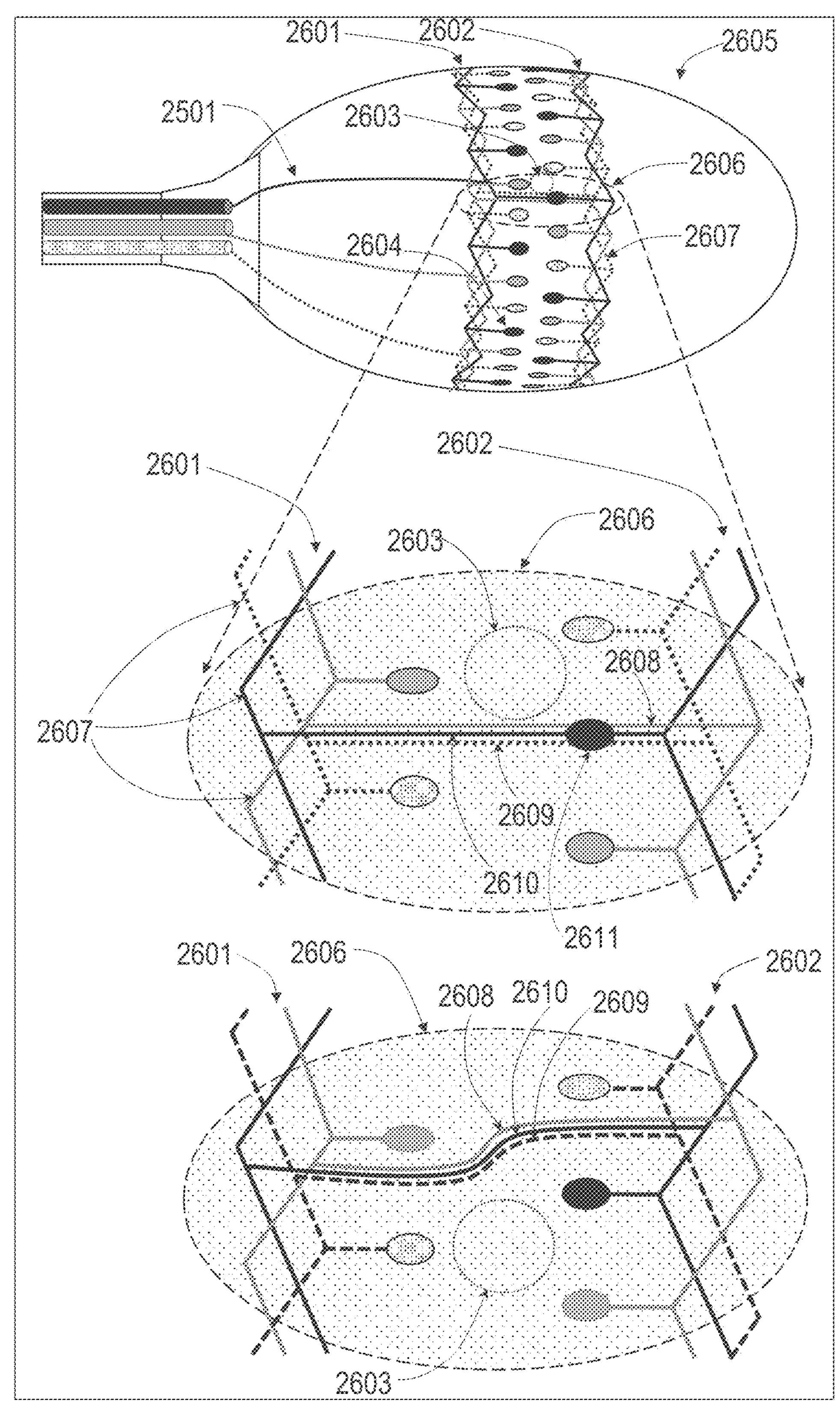
FIG. 26 is a schematic illustration, similar to that illustrated in FIG. 25, but with a bounded area that can be free of electrically conductive interconnection wires.

FIG. 26 is a schematic illustration of locally interconnected REF electrodes, similar to that illustrated in FIG. 25, but showing in FIG. 26 an arrangement in which the area 2603 bounded by a particular triad of electrodes is free of electrically conductive interconnection wires carrying individual REF signals to individual REF electrodes in the triad. This can help reduce or avoid distortion of the applied REF in an area 2603 of interest for applying the REF directed toward nearby biologic tissue.

In the illustrative example of FIG. 26, the proximal ring of REF electrodes 2601A, 2601B, 2601C can have like triad members being electrically selectively interconnected by corresponding even more proximal local circumferential electrically conductive like-triad member-specific interconnects 2607, each of which can be more proximal to the lead body of the REF catheter 1704 than the corresponding REF electrodes 2601A, 2601B, 2601C. The proximal local circumferential electrically conductive like-triad member-specific interconnects 2607 can respectively include corresponding longitudinally and proximally running interconnect traces 2501, such as which can, in turn, individually respectively electrically connect to the electrically conductive wires 1801, 1802, 1803 in the lead body of the REF catheter 1704.

In the illustrative example of FIG. 26, the distal ring of REF electrodes 2602A, 2602B, 2602C can have like triad members being electrically selectively interconnected by corresponding even more distal local circumferential electrically conductive like-triad member-specific interconnects 2607, each of which can be more distal to the lead body of the REF catheter 1704 than the corresponding REF electrodes 2602 forming a distal ring. Because the proximal ring of REF electrodes 2601 are located between the distal ring of REF electrodes 2602 and the lead body of the REF catheter 1704, electrically conductive wires 1801, 1802, 1803, at least one (or only one) set of proximal-ring-to-distal-ring electrical interconnections 2608, 2609, 2610 can be placed in close lateral circumferential proximity to one another (to minimize the composite field generated by the REF signals carried by said connections) to interconnect individual ones of the proximal like-triad member-specific interconnects 2607 to corresponding individual ones of the distal like-triad member-specific interconnects 2607.

Figure 27:
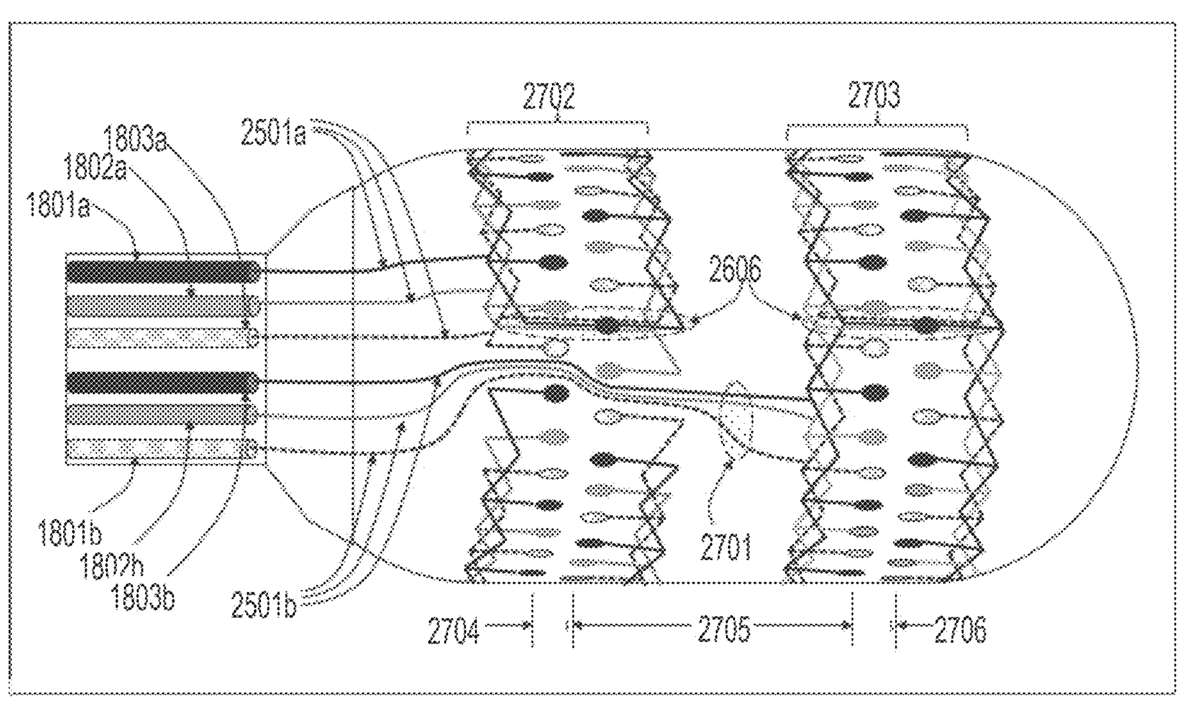
FIG. 27 is a schematic illustration similar to what is shown in FIG. 26, but showing a dual band or dual drive version.

FIG. 27 is a schematic illustration similar to what is shown in FIG. 26, but showing a dual band or dual drive version, in which dual sets of REF signals 701A, 702A, 703A and 701B, 702B, 703B can be independently provided, such as via individual ones of dual triad sets of electrically conductive wires 1801A, 1802A, 1803A and 1801B, 1802B, 1803C, each set extending longitudinally through the lead body of the REF catheter 1704. A first proximal pair of rings of REF electrodes 2702 can be located as shown and similarly described with respect to FIG. 26. A second distal pair of rings of REF electrodes 2703 can be located more distally than the first proximal pair of rings of REF electrodes 2702, and interconnection routing can be arranged analogously to that described with respect to FIG. 26, but with an additional set of at least one (or only one) set of electrical interconnections 2701 that can be placed in close lateral circumferential proximity to one another (to minimize the composite field generated by the REF signals carried by said connections) to interconnect to individual ones of a first proximal ring pair of REF electrodes 2702 and the more distal second pair of rings of REF electrodes 2703.

In such a dual-band, dual-drive example, the device shown in FIG. 27 can be used to concurrently treat both the antra and ostia of a pulmonary vessel. The fixed distance 2705 between the proximal pair of rings of REF electrodes 2702 and the distal pair of rings of REF electrodes 2703 can be selectively sized to replicate an expected distance between the antra and ostia of a pulmonary vessel such that both targeted regions can be treated simultaneously.

Figure 28:
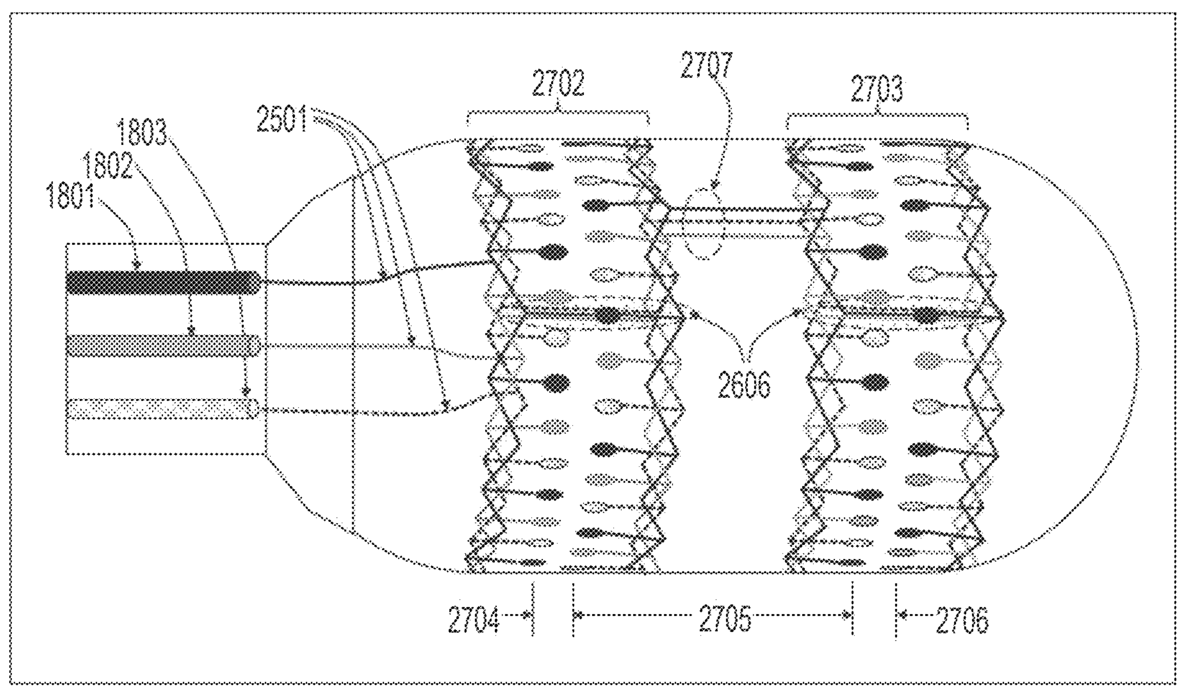
FIG. 28 is a schematic view, showing one specific subset of the arrangement shown in FIG. 27, suitable when driving the distal and proximal pairs of rings with the same voltage signals.

FIG. 28 is a schematic view, similar to that shown in FIG. 27, but showing one specific subset of the arrangement shown in FIG. 27, which is suitable when the distal pair of rings is to be driven with the same voltage signals as the proximal pair of rings, in which case respective ones of conductors 1801*b*, 1802*b*, 1803*b* can be combined with the equivalent conductor 1801*a*, 1802*a*, 1803*a* such that only three lead body conductor wires would be needed to drive the proximal and distal ring pairs, such as shown in FIG. 28. The interconnect between proximal and distal REF electrode ring pairs would remain as in FIG. 26.

Figure 29:
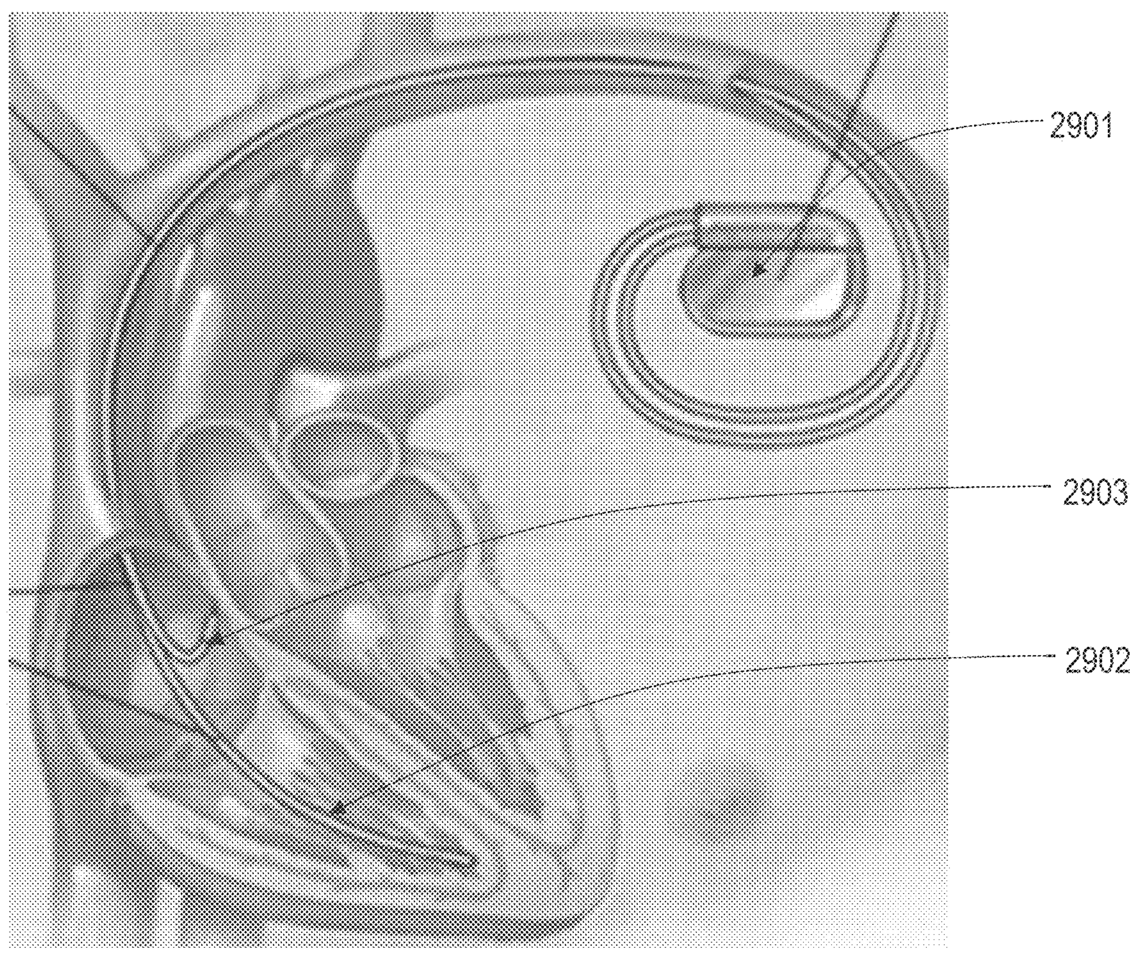
FIG. 29 shows an example of an implantable pulse generator (IPG) and a connected intravascular lead system, such as for delivering REF therapy.

FIG. 29 shows an example of an implantable pulse generator IPG 2901 and, connected thereto, an intravascular lead system, such as which can include a ventricular lead 2902, such as which can be capable of carrying pacing, defibrillation, cardioversion, sensing, or other lead electrodes, and an atrial lead 2903, which can similarly be capable of carrying such electrical therapy electrodes.

Using the arrangement shown in FIG. 29, cardioversion or defibrillation can be applied to the heart, such as using a configuration of three electrodes, which can respectively be located at a distal end of the ventricular lead 2902, at a distal end of the atrial lead 2903, and at the housing ("can") of the IPG 2901. Conventionally, electrodes are in physical and electrical contact with tissue, and the electrotherapy delivered via these electrodes causes charge carriers to pass through the intervening tissue as electrically conducted "bulk" current, as opposed to "displacement" current via capacitive application of REF therapy using the REF electrodes, such as described above. However, the electrodes shown in the arrangement of FIG. 30 can be overlaid with a thin dielectric insulator to permit such capacitive application of REF therapy for cardioversion or defibrillation, such as described above with a focus on (but not limited to) tissue ablation.

The particular positioning of the leads in FIG. 29 is dependent on the anatomy of the patient. Therefore, the distances and angles between the electrodes carried by the leads and the IPG are not uniform. Using the arrangement of FIG. 29, the therapeutic electric fields will need to be adjusted to effectively generate an appropriate therapeutic electric field in the area of interest.

To provide this adjustability, the present system can employ augmented processing and control in an augmented IPG 2901. The augmented IPG can include programmed or other control or signal processing such as can employ one or more low level calibration signals (e.g., impedance measurement signals or the like) such as to help determine or estimate the distance between pairs of electrodes, from which the resulting angles between electrode pairs can also be determined. This electrode distance information, electrode angle information, or both, can then be used to adjust one or both of a signal amplitude and phasing or timing of cardioversion or defibrillation electrical therapy signals, such that the resulting REF vector can be applied in a controlled and specified manner, as desired, for improved efficacy of cardioversion, defibrillation, or other therapy.

FIGS. 30A-30D show examples of various electrode configurations, such as which can be employed using the present techniques for applying REF therapy capacitively via a triad of REF electrodes. In FIGS. 30A-30D, at least one of the REF electrodes can be located on the IPG housing or "can" of the IPG 2901, while others of the electrodes can be located upon one or more intravascular catheters or "leadwires," for example, such as shown and described with respect to FIGS. 30A-30D.

Figure 30A:
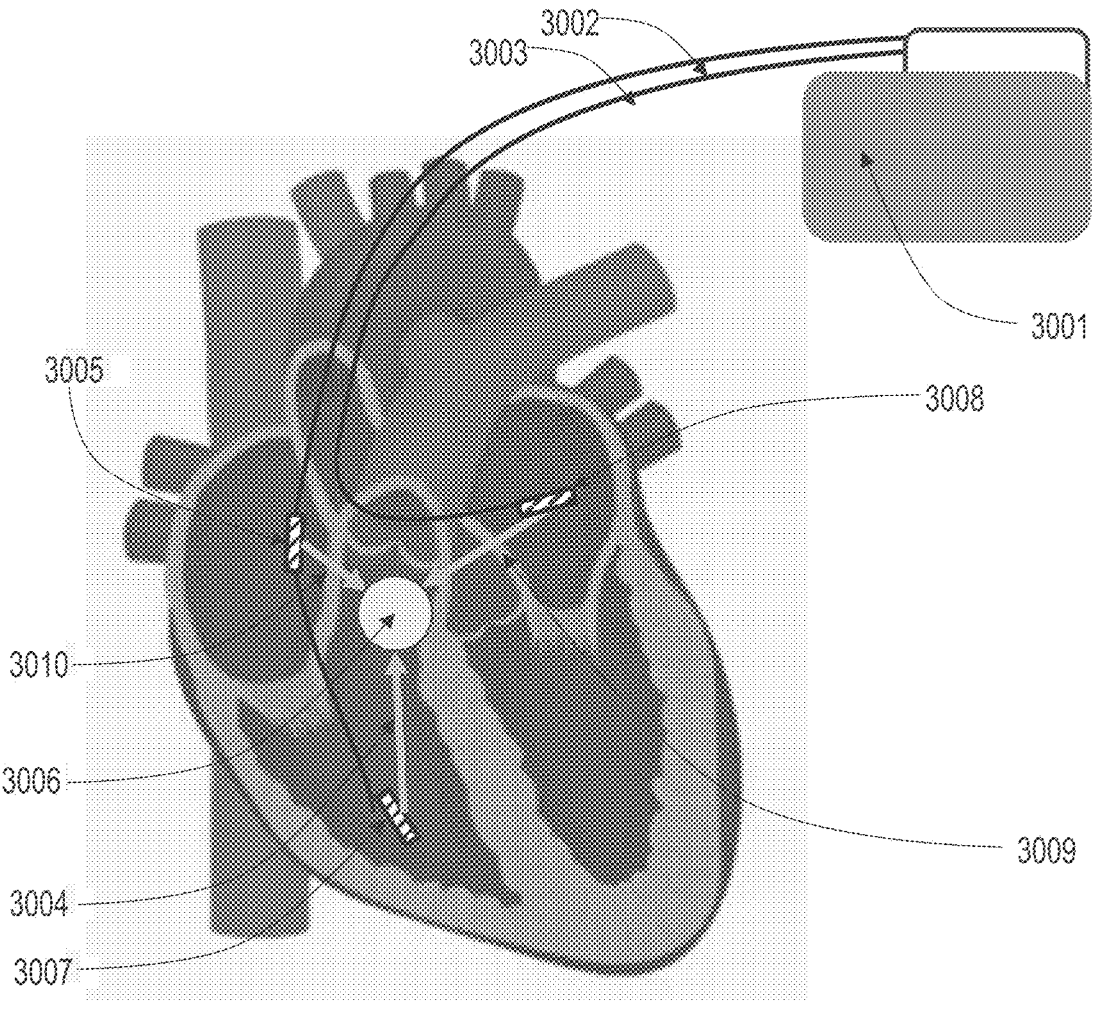
FIGS. 30A-30D show examples of various electrode configurations, such as which can be employed using the present techniques for applying REF therapy capacitively via a triad of REF electrodes.

In FIG. 30A, the REF therapy system can include an IPG 2901. The IPG 2901 can include a hermetically-sealed electrically conductive housing or "can." The housing or "can" be partially or fully covered with an overlying electrical insulator. The thickness of this electrical insulator layer overlying the housing or "can" of the IPG 2901 can vary. For example, a region of the housing of the IPG 2901 intended to be used as an REF electrode, such as for capacitive delivery of REF therapy, can have a thinner insulating dielectric than one or more other regions of the housing of the IPG 2901 that are not intended to be used as an REF electrode for capacitive delivery of REF therapy.

In FIG. 30A, a right ventricular (RV) intravascular catheter leadwire 3002 can include a proximal end coupled to the IPG 2901, and a distal end positioned to be located in the RV of a heart, such as at or near an RV apex. The RV leadwire 3002 can include a distal RV REF electrode 3007 located at or near its distal end, such as can be positioned in the RV of the heart, such as at or near the RV apex. Spaced apart more proximally on the same RV leadwire 3002 from the distal RV REF electrode 3007 can be a right atrial (RA) REF electrode 3011, such that the RA REF electrode 3011 can be located in an RA of the heart.

In FIG. 30A, a left ventricular or coronary sinus (LV/CS) intravascular catheter leadwire 3003 can include a proximal end coupled to the IPG 2901, and a distal end positioned to be located near the LV of a heart, such as in a coronary sinus (CS) accessible intravascularly from the right side of the heart, but extending within the heart muscle in close proximity to the LV the heart. The LV/CS leadwire 3003 can include a distal CS REF electrode 3008 located at or near its distal end, such as can be positioned within the CS and in close proximity to the LV of the heart.

In the arrangement of FIG. 30A, an REF electrode triad can be formed by the RV electrode 3007, the RA electrode 3005, and the CS electrode 3008. This REF electrode triad can be used to target a desired target region 3006 to which an REF therapy can be delivered, such as to provide cardioversion or defibrillation REF, such as instead of or in addition to a cardioversion or defibrillation countershock. As explained earlier, these electrodes in this REF electrode triad may not be equidistant from each other. Accordingly, the respective REF signals being provided by the RSG 1701 may be adjusted, such as to "normalize" the REF in the desired target region 3006, such as by adjusting any one or more of an amplitude, phase, timing, or frequency of one or more individual REF signals being provided to respective ones of the RV electrode 3007, the RA electrode 3005, and the CS electrode 3008 in the REF electrode triad. Such adjustment can be based on measured interelectrode distance between pairs of electrodes, the angles of the triangle formed by the REF electrode triad, or both of these.

Figure 30B:
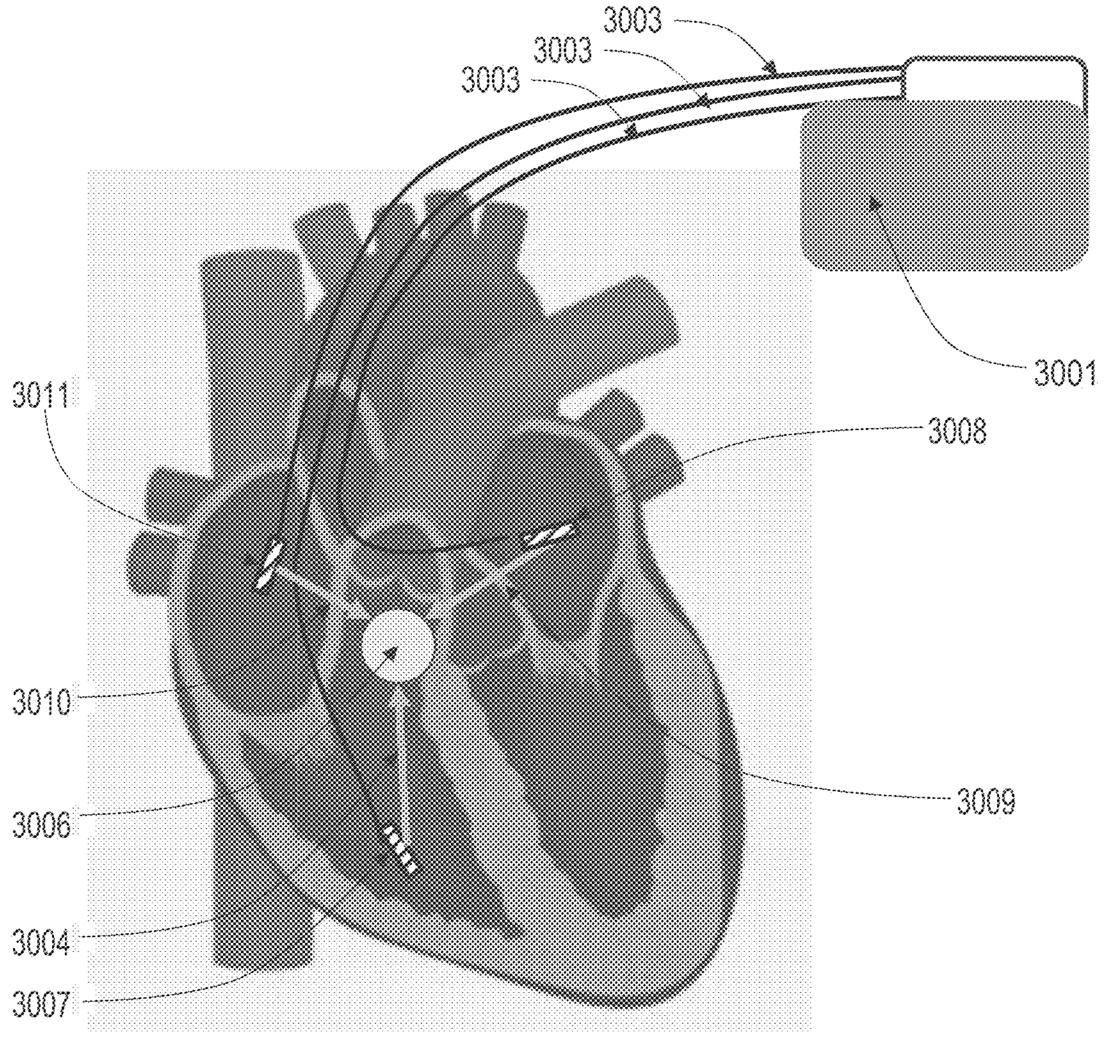

In FIG. 30B, the REF therapy system can include an IPG 2901, similar to that described above with respect to FIG. 30A.

In FIG. 30B, a right ventricular (RV) intravascular catheter leadwire 3002 can include a proximal end coupled to the IPG 2901, and a distal end positioned to be located in the RV of a heart, such as at or near an RV apex. The RV leadwire 3002 can include a distal REF electrode 3007 located at or near its distal end, such as can be positioned in the RV of the heart, such as at or near the RV apex. A separate right atrial (RA) leadwire 3003 can also include a right atrial (RA) REF electrode 3011, such as at or near its distal end, such that the RA REF electrode 3011 can be located in an RA of the heart.

In FIG. 30B, a left ventricular or coronary sinus (LV/CS) intravascular catheter leadwire 3003 can include a proximal end coupled to the IPG 2901, and a distal end positioned to be located near the LV of a heart, such as in a coronary sinus (CS) accessible intravascularly from the right side of the heart, but extending within the heart muscle in close proximity to the LV the heart. The LV/CS leadwire 3003 can include a distal CS REF electrode 3008 located at or near its distal end, such as can be positioned within the CS and in close proximity to the LV of the heart.

In the arrangement of FIG. 30B, an REF electrode triad can be formed by the RV electrode 3007, the RA electrode 3005, and the CS electrode 3008. This REF electrode triad can be used, such as explained above with respect to FIG. 31, to target a desired target region 3006 to which an REF therapy can be delivered, such as to provide cardioversion or defibrillation REF.

Figure 30C:
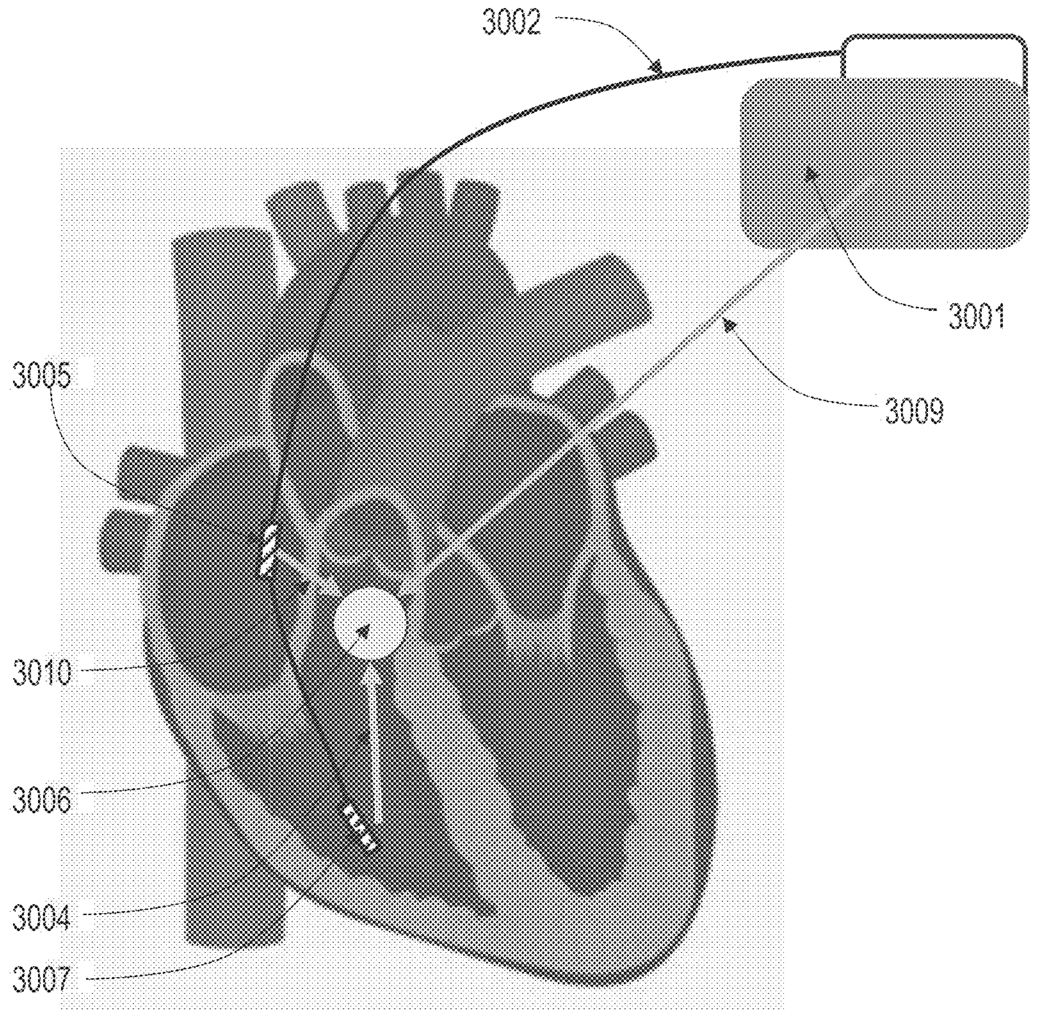

In FIG. 30C, the REF therapy system can include an IPG 2901, similar to that described above with respect to FIG. 30A.

In FIG. 30C, a right ventricular (RV) intravascular catheter leadwire 3002 can include a proximal end coupled to the IPG 2901, and a distal end positioned to be located in the RV of a heart, such as at or near an RV apex. The RV leadwire 3002 can include a distal REF electrode 3007 located at or near its distal end, such as can be positioned in the RV of the heart, such as at or near the RV apex. A separate right atrial (RA) leadwire 3003 can also include a right atrial (RA) REF electrode 3011, such as at or near its distal end, such that the RA REF electrode 3011 can be located in an RA of the heart.

In FIG. 30C, an REF electrode on the housing or "can" of the IPG 2901 can be used to generate its triad component of an REF electric field, such as from a pectoral or other implantation location of the IPG 2901. Thus, in the arrangement of FIG. 30C, an REF electrode triad can be formed by the RV electrode 3007, the RA electrode 3005, and a can electrode located on the housing or can of the IPG 2901. This REF electrode triad can be used, such as explained above with respect to FIG. 30A, to target a desired target region 3006 to which an REF therapy can be delivered, such as to provide cardioversion or defibrillation REF.

Figure 30D:
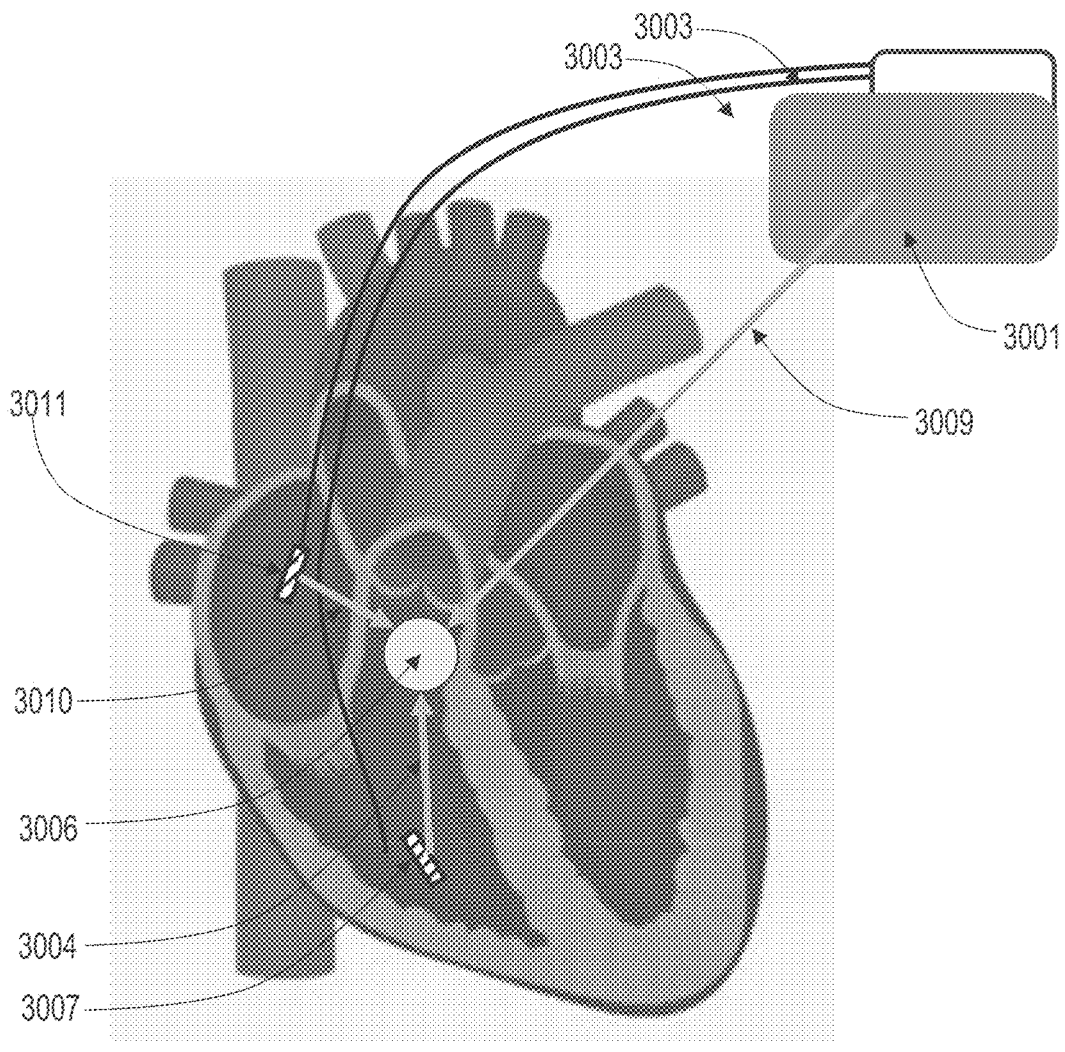

In FIG. 30D, the REF therapy system can include an IPG 2901, similar to that described above with respect to FIG. 30A.

In FIG. 30D, a right ventricular (RV) intravascular catheter leadwire 3002 can include a proximal end coupled to the IPG 2901, and a distal end positioned to be located in the RV of a heart, such as at or near an RV apex. The RV leadwire 3002 can include a distal REF electrode 3007 located at or near its distal end, such as can be positioned in the RV of the heart, such as at or near the RV apex. A separate right atrial (RA) leadwire 3003 can also include a right atrial (RA) REF electrode 3011, such as at or near its distal end, such that the RA REF electrode 3011 can be located in an RA of the heart.

In FIG. 30D, an REF electrode on the housing or "can" of the IPG 2901 can be used to generate its triad component of an REF electric field, such as from a pectoral or other implantation location of the IPG 2901. Thus, in the arrangement of FIG. 30D, an REF electrode triad can be formed by the RV electrode 3007, the RA electrode 3005, and a can electrode located on the housing or can of the IPG 2901. This REF electrode triad can be used, such as explained above with respect to FIG. 30A, to target a desired target region 3006 to which an REF therapy can be delivered, such as to provide cardioversion or defibrillation REF.

Figure 31:
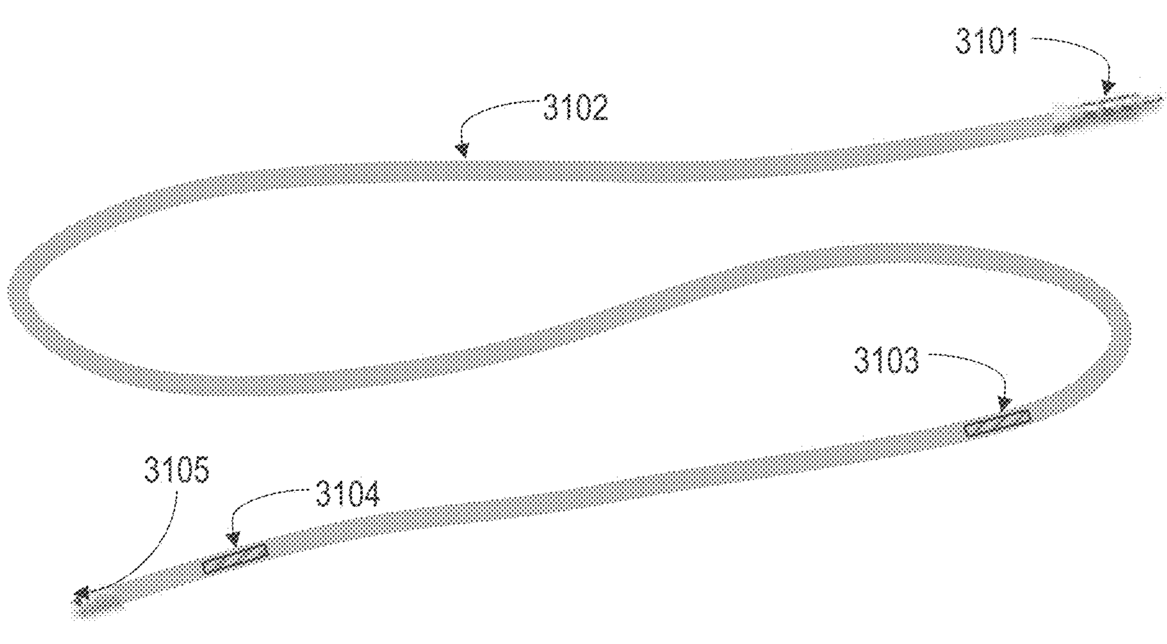
FIG. 31 is a schematic view of an example of an intravascular catheter leadwire that can include three REF electrodes.

FIG. 31 is a schematic view of an example of an intravascular catheter leadwire 6030 that can include three REF electrodes. This can include: (1) a distal tip REF electrode 3105; (2) a distal body REF electrode 3104, such as which can be located on the lead body of the intravascular catheter leadwire 3102 and located slightly proximally of the distal tip electrode 3104; and (3) a proximal body REF electrode 3103, such as can be appropriately spaced proximally on the intravascular catheter leadwire 3003 to be located in a right atrium (RA) when the distal tip REF electrode 3105 is located at or near an apex of a right ventricle (RV) of the heart of the patient. The multi-filar intravascular catheter leadwire 3102 can include corresponding longitudinally extending individual wires, such as which can be electrically coupled to these REF electrodes, and electrically coupled to corresponding individual terminals of a ring connector 3101, such as which can be located at a proximal end of the multi-filar intravascular catheter leadwire 3102 for electrically coupling to a corresponding terminal of a header of the IPG 2901.

Figure 32:
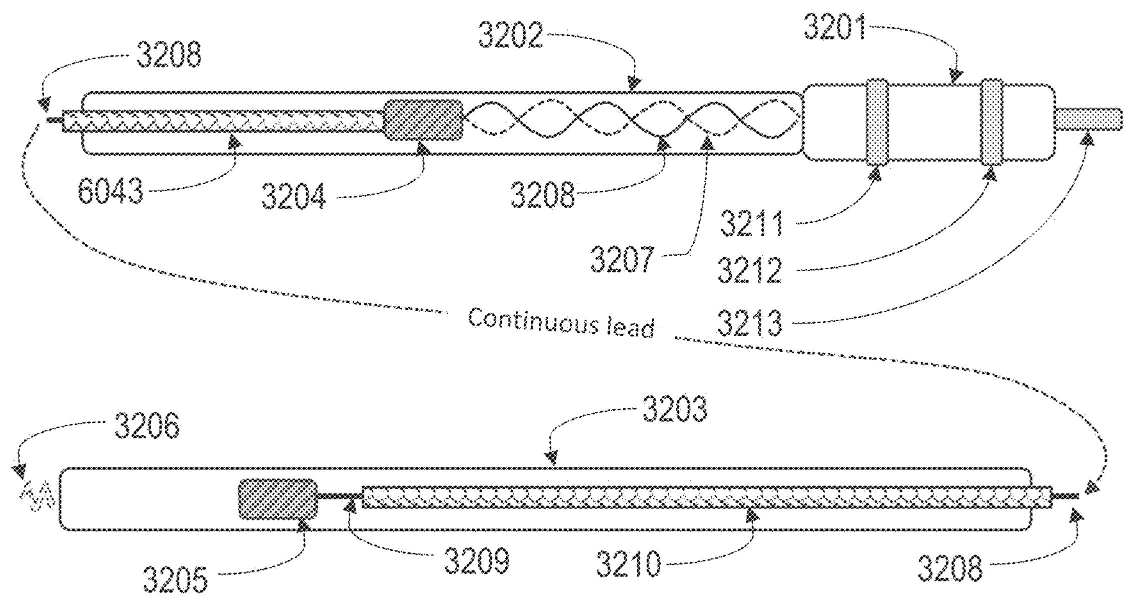
FIG. 32 is a cross-sectional schematic view of an example of an intravascular catheter leadwire that can include two REF electrodes.

FIG. 32 is a cross-sectional schematic view of an example of an intravascular catheter leadwire 3003 including two REF electrodes. In this example a distal tip can include an active affixation device 3206, which need not serve as an REF electrode. A distal body electrode 3205 can be located slightly proximal of the distal tip active affixation device 3206. A proximal body electrode 3204 can be appropriately spaced proximally on the intravascular catheter leadwire 3003 such as to be located in a right atrium (RA) when the distal body electrode 3205 is located in a right ventricle (RV) of the heart of the patient. The multi-filar intravascular catheter leadwire can include corresponding longitudinally extending individual wires, such as which can be electrically coupled to these electrodes, and electrically coupled to corresponding individual terminals of a ring connector 3201, such as which can be located at a proximal end of the multi-filar intravascular catheter leadwire for electrically coupling to a corresponding terminal of a header of the IPG 2901.

Figure 33:
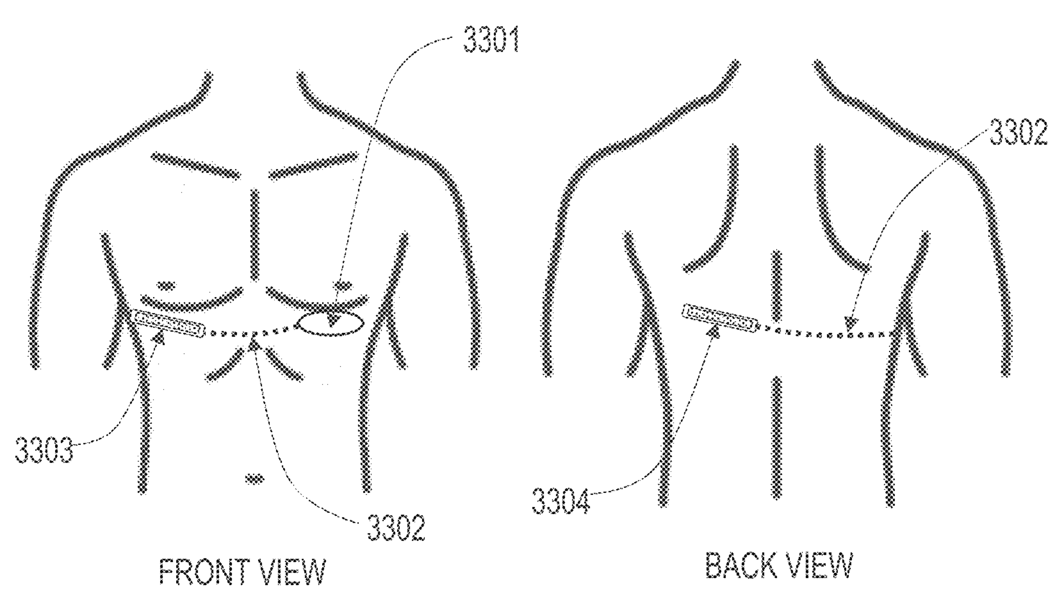
FIG. 33 is a schematic view illustrating generally an example of a placement of a subcutaneous ("Sub-Q") implantable cardioverter defibrillator (ICD) including a Sub-Q IPG to deliver REF therapy.

FIG. 33 is a schematic view illustrating generally an example of a placement of a subcutaneous ("Sub-Q") implantable cardioverter defibrillator (ICD) including a Sub-Q IPG 3301, such as which can employ REF therapy to deliver capacitively-coupled cardioversion or defibrillation therapy, e.g., without requiring electrodes that actually physically touch tissue and deliver bulk current to effect a cardioversion or defibrillation countershock.

In FIG. 33, a Sub-Q ICD IPG 3301 can be subcutaneously implanted into a patient, without requiring intravascular catheter leadwires extending intravascularly into the heart, but instead providing at least two Sub-Q REF electrodes 3304, 3303 remote from but physically and electrically connected to the IPG 3301, which provides a third Sub-Q electrode for completing a Sub-Q REF electrode triad for delivering REF therapy to a targeted area of biological tissue, such as toward arrhythmogenic cardiac tissue prone to experiencing a cardiac arrythmia. As explained with respect to FIGS. 29 and 30A-30D, the electrodes may not form a perfect equilateral triangle about the targeted area to be treated by REF therapy. Accordingly, the REF signals delivered to the individual electrodes of the Sub-Q electrode triad can be normalized, as similarly explained elsewhere in this document, but particular to a Sub-Q arrangement, such as that occurring in a particular patient being treated by the REF therapy. As explained above, such normalization or adjustment can be based upon measured distances between pairs of electrodes in the Sub-Q electrode triad, based upon angles in the triangle formed by such a triad of electrodes at its vertices, or based upon both of these. In an example, the Sub-Q electrode sizes, shapes, and structures can be selected to concentrate the REF therapy energy throughout the heart during REF therapy session.

The first and second remote Sub-Q electrodes can cooperate with the electrode at the Sub-Q ICD IPG 3301, such as to generate an electric field that can be characterized by a rotating voltage gradient across a substantial portion of the heart of a patient, when the first and second electrodes have been implanted at respective first and second Sub-Q locations within the patient.

The voltage on the individual REF electrodes in the triad such as to impose a rotating electric field of sufficient intensity across at least a portion of a heart to defibrillate the heart. In an example, the system can be configured such that REF electric field has a voltage gradient that is in a range between 3 Volts per centimeter and 8 Volts per centimeter across the desired arrhythmic region of cardiac tissue.

The first and second remote Sub-Q electrodes can be adapted, configured, or arranged such as to be implanted in the same plane that can be defined to be perpendicular to the patient's defined central longitudinal axis. The first and second remote Sub-Q electrodes can be adapted to be implanted at desired locations such as to generate an electric field in a defined plane that is desired to pass through at least a portion of the heart, such as through a center of the heart. The first and second remote Sub-Q electrodes can optionally be formed or provided with rounded edges and without sharp corners, such as to help ensure that the electric field between these electrodes is not concentrated at any such edges of any such electrodes.

The first and second remote Sub-Q electrodes can cooperate with a third electrode at the Sub-Q ICD IPG 3301, with the individual electrodes in the triad being provided with individually tailored electrical signals from by REF Signal Generator (RSG) 1701 housed within the Sub-Q ICD IPG 3301. In an example, a resulting REF can be generated through the heart, such the electric field characterized by substantially parallel electric field lines extending across a substantial portion of the heart of the patient when the Sub-Q ICD IPG 3301 housing is implanted in a plane that is defined to be perpendicular to the patient's defined central longitudinal axis with this planed passing through the patient's sternum.

The Sub-Q ICD IPG 3301 can include sensing circuitry, such as which can be connected to separate electrically uninsulated sensing electrodes, which can be co-located with or near the electrically-insulating REF electrodes, such as for sensing or detecting intrinsic or induced cardiac signals. Such cardiac signal sensing can be used to detect intrinsic or evoked cardiac activity, such as which can an arrhythmia to be responsively treated by delivering the REF therapy, such that the REF therapy can be triggered in response to detected arrhythmic cardiac activity.

Figure 34:
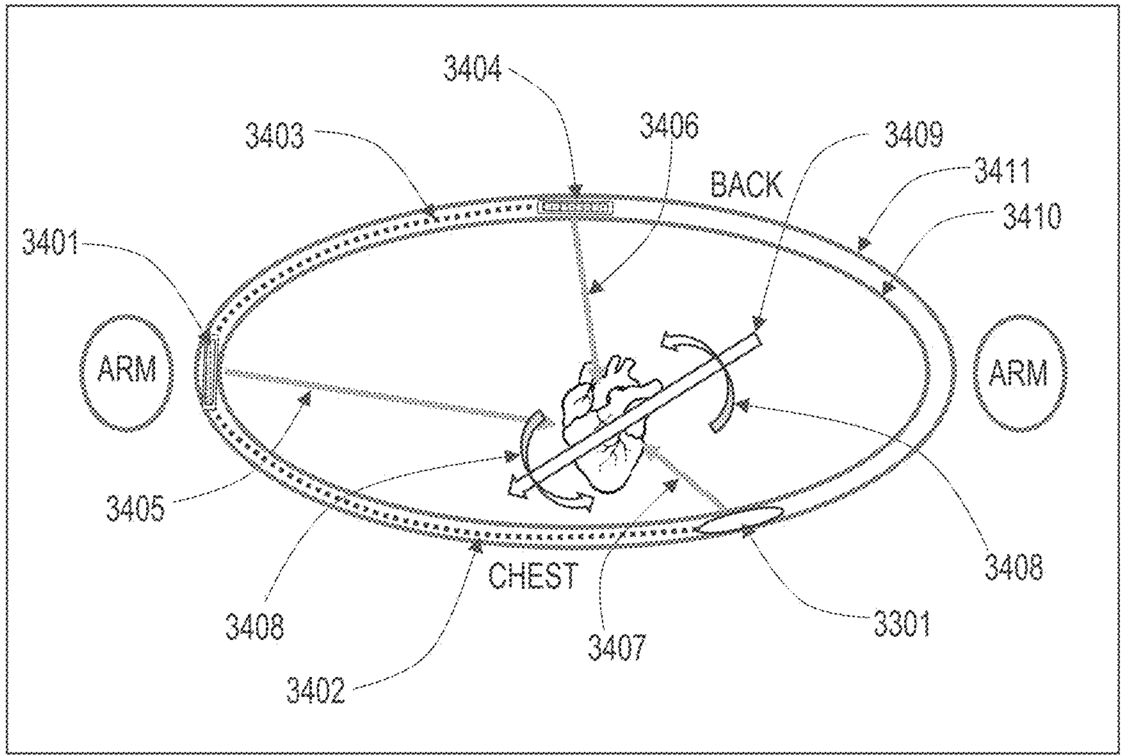
FIG. 34 is a schematic illustration of an example of the Sub-Q approach described above with respect to FIG. 33.

FIG. 34 is a schematic illustration of an example of the Sub-Q approach described above with respect to FIG. 33. FIG. 34 further shows an example of an REF plane that can be defined by first and second remote Sub-Q electrodes that can cooperate with a third electrode at the Sub-Q ICD IPG 3301. The patient's heart, arms, chest, and back, are annotated in FIG. 34.

Figure 35:
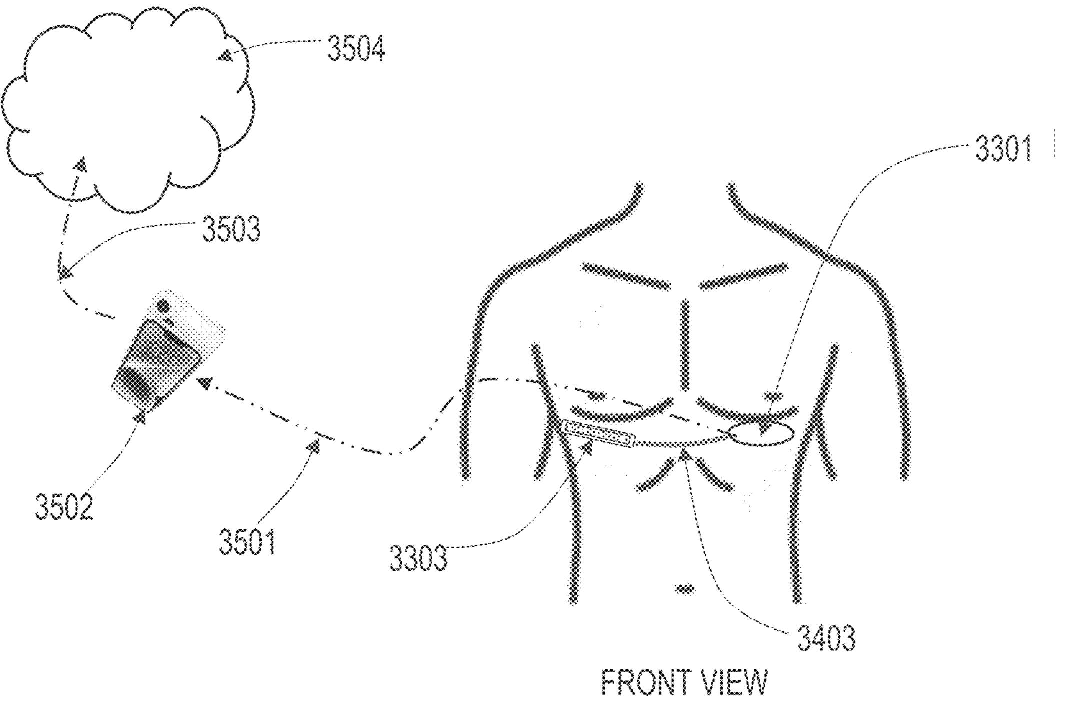
FIG. 35 is a schematic illustration of an example of the Sub-Q approach described above with respect to FIGS. 33-34, showing communication to a local or remote auxiliary interface device.

FIG. 35 is a schematic illustration of an example of the Sub-Q approach described above with respect to FIGS. 33-34, showing an embodiment in which the sensed cardiac signals or other information can be wireless communicated from the Sub-Q ICD IPG 3301 to a local user interface device, such as a smartphone or other computing device 3502, which, in turn, can communicate with further signal processing, control, and memory componentry that can be more remotely located in the "cloud," such as for allowing one or more of remote monitoring, remote diagnosis, or remote control, such as by a physician or other caregiver, or by an artificial-intelligence (AI) assisted or other remote device.

Figure 36:
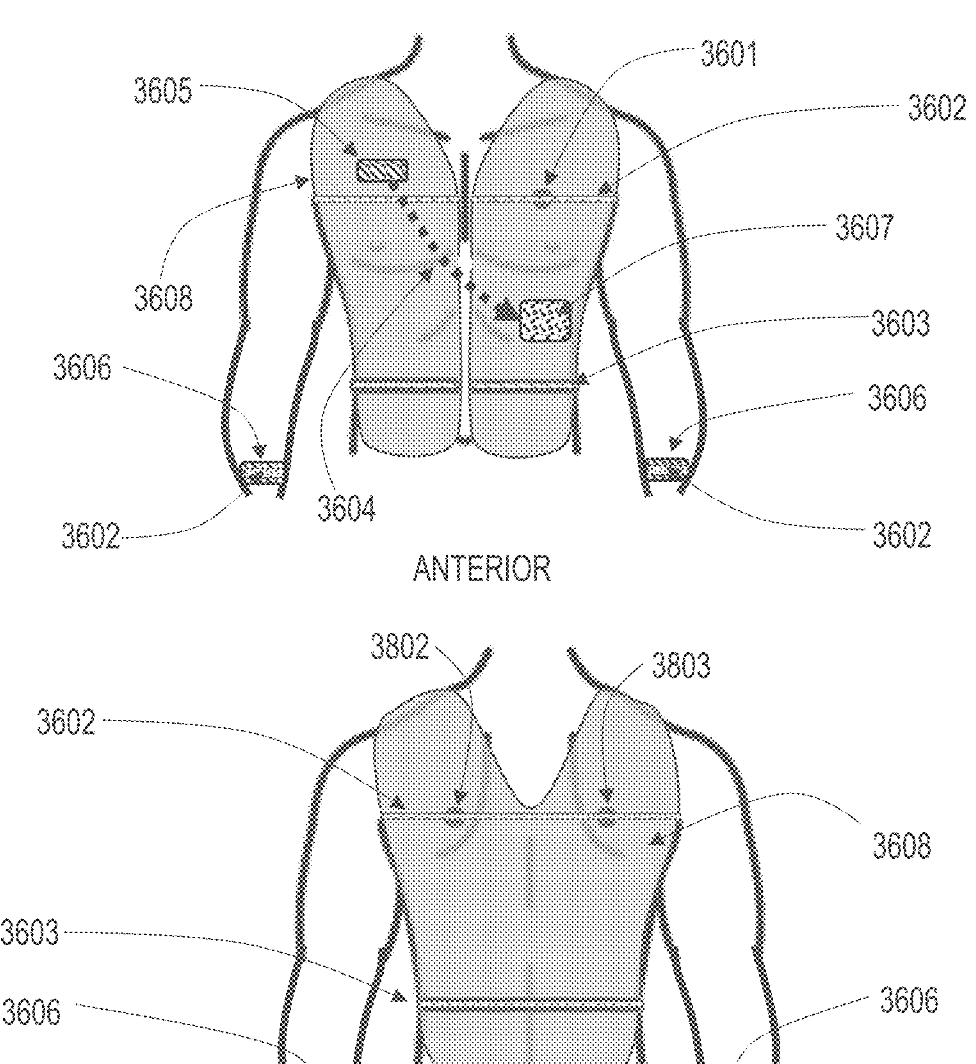
FIG. 36 is a schematic view illustrating generally a wearable cardioverter defibrillator that can employ REF therapy.

FIG. 36 is a schematic view illustrating generally an example of a placement of an externally wearable (e.g., via a vest, a jacket, or another garment, via a strap, or via an adhesively-affixable skin-wearable substrate, or the like) cardioverter defibrillator, such as which can employ REF therapy to deliver capacitively-coupled cardioversion or defibrillation therapy, e.g., without requiring electrodes that actually physical touch tissue and deliver bulk current to effect a cardioversion or defibrillation countershock.

FIG. 36 shows an example in which an article of clothing such as a vest 3608 can be sized, shaped, or otherwise be configured such as to be worn around the upper thorax, e.g., as a jacket or vest 3608. In the example of FIG. 36, the vest 3608 can carry a triad of three electrically-insulated REF electrodes 3601, 3802, 3803. The REF electrodes 3601, 3802, 3803 can be embedded within the vest 3608, for example, so as to be individually located both in the posterior and anterior areas with respect to the patient wearing the vest 3608. The REF electrodes 3801, 3802, 3803 can be electrically insulated from the patient or other wearer. The vest 3608 can be configured to arrange the REF electrodes 3801, 3802, 3803 to define a plane that can intersect a center or at least a portion of the heart of the patient.

Additionally, sensors 7026, 7028 can employ at least partially electrically-uninsulated electrodes that can be arranged (e.g., by the vest 3608, by a wearable adhesive skin patch, or otherwise) to physically contact the skin of the patient such as to detect one or more intrinsic or evoked cardiac signals and deliver the detected cardiac signals, such as through hardwired electrical connections, or via a wireless transceiver such as which can provide a wireless communication link to a signal processor or controller carried by the vest 3608. The signal processor or controller can perform programmed instructions, such as to analyze the one or more cardiac signals, to determine appropriate REF therapy such as to counter a cardiac arrhythmia, and to control delivery of the REF therapy via the REF electrodes 3801, 3802, 3803.

Figure 37:
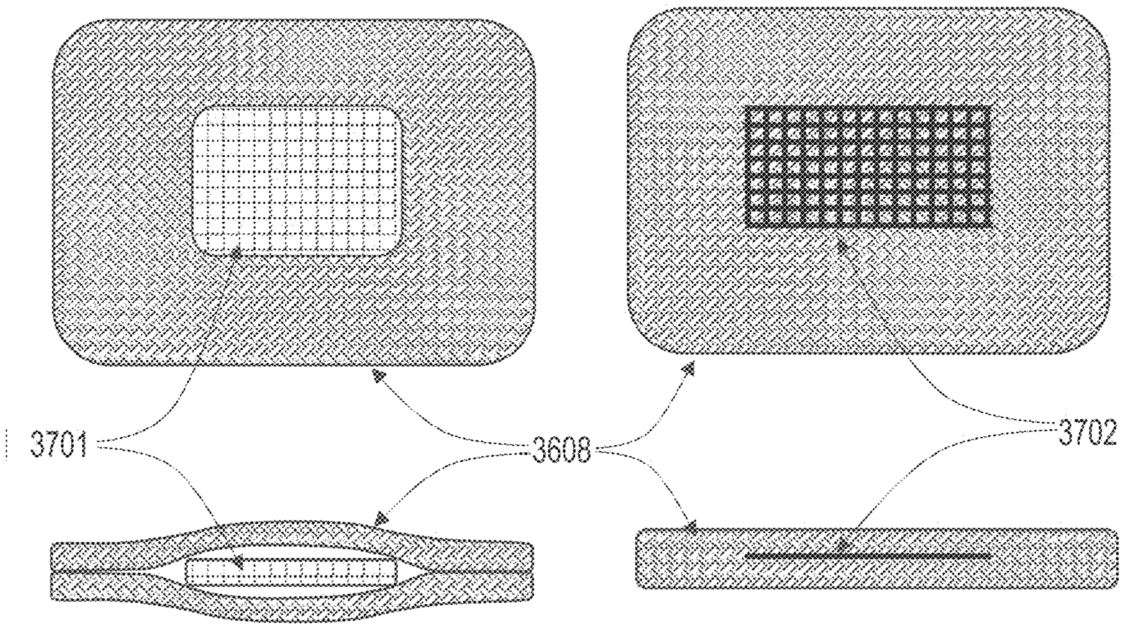
FIG. 37 is a schematic illustration showing an example of how REF electrodes can be embedded within layers of fabric or other material of the vest.

FIG. 37 is a schematic illustration showing an example of how the REF electrodes 3801, 3802, 3803 can be embedded within layers of fabric or other material of the vest 3608 or other garment. Because the REF electrodes 3801, 3802, 3803 do not need to be in direct contact with skin of the patient wearer of the vest 3608, these REF electrodes 3801, 3802, 3803 can be embedded in the fabric layers 7043 of the vest 3608, such as shown in FIG. 37. Since the energy delivered via REF therapy is delivered via ultra-low displacement currents, instead of via bulk electrical current transporting charge carriers through tissue, the electrical conductors associated with the corresponding REF electrodes 3801, 3802, 3803 can be small and thin in diameter or other lateral cross-sectional area, such as shown in FIG. 37. In an example, the interconnections between REF electrodes 3801, 3802, 3803 and the corresponding signal processor or controller can include or can be comprised of very fine (e.g., narrow diameter or small cross-sectional area) electrical conductors that can optionally be incorporated into the fabric of the vest 3608. Therefore, the vest 3608 can be light weight and flexible-both of which improve the comfort for the wearer. This, in turn, can help improve the probability that the patient will wear the vest 3608 as directed by the clinician. In addition, since the REF electrodes 3801, 3802, 3803 do not need to be in direct electrical contact with the skin of the patient, there is no need for using gels or other conductive materials to help improve delivery of the therapy.

Although the delivery of REF therapy does not require direct electrical contact of the REF electrodes 3801, 3802, 3803 to the patient's skin, decreasing the distance between the REF electrodes 3801, 3802, 3803 and the patient's skin can help increase the amount of energy delivered by the REF into the thorax of the patient, which can help improve effectivity of the REF therapy. Such decreased distance between the REF electrodes 3801, 3802, 3803 and the patient's skin can be facilitated by using one or more elastic bands 7010, for example, such as to bias the REF electrodes 3801, 3802, 3803 toward the patient's skin. Intrinsic or evoked cardiac signal (e.g., ECG) sensing can be provided in a number of ways, such as can include a separate ECG monitoring skin patch with sensing electrodes that are uninsulated and exposed to contact the patient's skin. Such cardiac signal sensing can optionally be incorporated into the present system by including an independent ECG sensing unit that can include a wireless transceiver allowing it to be communicatively coupled wirelessly by a wireless communication link 7024 to the main signal processor or controller 3607, such as to determine whether an arrhythmia treatable by REF therapy is present, to provide timing information for synchronizing the delivery of REF therapy, or the like.

Figure 38:
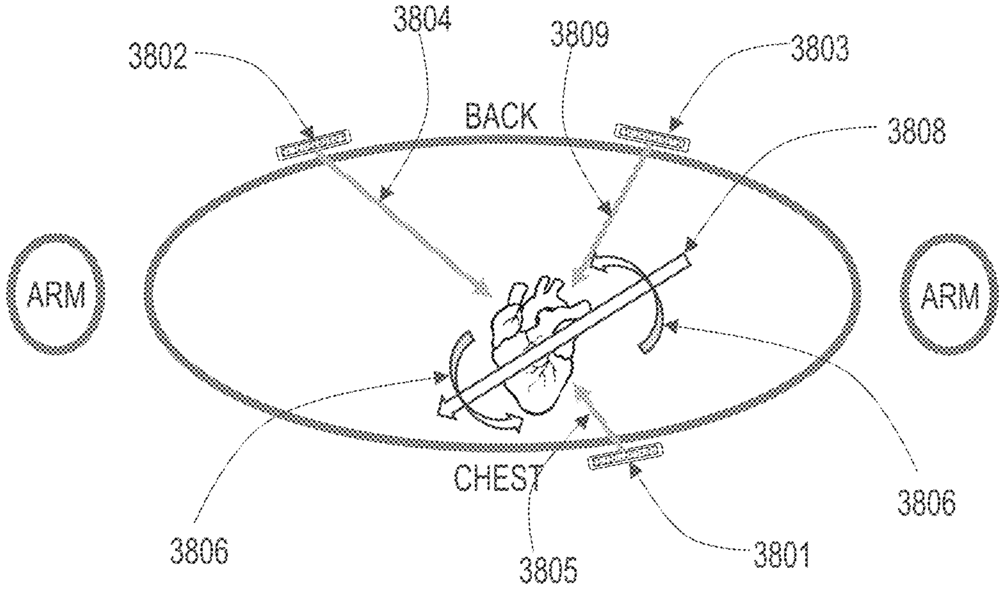
FIG. 38 is a schematic illustration, such as described above with respect to FIGS. 36-3, showing an REF plane that can be defined by external REF electrodes.

FIG. 38 is a schematic illustration of an example of the external wearable approach to REF therapy, such as described above with respect to FIGS. 36-37. FIG. 38 further shows an example of an REF plane that can be defined by externally wearable REF electrodes 3801, 3802, 3803. The patient's heart, arms, chest, and back, are annotated in FIG. 38. Respective voltage signals can be applied to the REF electrodes 3801, 3802, 3803, such as to create composite REF electric fields that extend in the plane defined by the triad of REF electrodes 3801, 3802, 3803.

An optional enhancement can include applying an additional voltage signal via an additional REF electrode to help redirect the horizontal REF field vectors to provide them with a vertical component, either positive or negative, which can be employed to obtain a 3-dimensional REF therapy effect instead of the 2-dimensional REF therapy coverage being provided in the plane defined by the triad of REF electrodes 3801, 3802, 3803.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of applying non-destructive electric field therapy to a biologic cardiac tissue target of a subject using a medical device, at an energy below a level causing permanent impact damage to the biologic tissue target, the method comprising:

generating respective individual first, second, and third electrical signals, having time-varying electrical signal amplitudes that are phase-shifted from each other;

concurrently delivering the generated phase-shifted first, second, and third individual electrical signals to respective corresponding individual electrodes in an arrangement of a set of at least three electrodes that are each located in association with but galvanically isolated from the biologic cardiac tissue target; and capacitively coupling a rotating electric field (REF) via the galvanically isolated electrodes to the biologic cardiac tissue target, the REF provided to the biologic cardiac tissue target by a superpositioned composite of respective phase-shifted components from corresponding concurrently-delivered time-varying first, second, and third electrical signal amplitudes that are phase-shifted from each other and delivered to the individual electrodes arranged in the set of at least three electrodes and thereby providing at least one of a cardioversion, defibrillation, pacing, or cardiac resynchronization stimulation energy to the biologic cardiac tissue target at the energy below the level causing permanent impact damage to the biologic cardiac tissue target.

2. The method of claim 1, further comprising:

specifying or selecting one or more parameters for generating the respective electrical signals specified to provide sufficient energy for capacitively coupling the REF via the galvanically isolated electrodes toward the biologic tissue target to treat the biologic tissue target via at least one of cardioversion, defibrillation, pacing, or cardiac resynchronization, wherein the electrodes are equidistant from each other in spacing and equally separated from one another in phase of the corresponding electrical signals applied to the electrodes.

3. The method of claim 2, further comprising specifying or selecting one or more parameters of each of the concurrently-delivered time-varying first, second, and third electrical signals, including at least one of time-varying signal cycle frequency, signal peak amplitude, signal morphology, phase delay between respective phase-shifted components, burst time duration, interburst time duration, number of cycles, or number of bursts and using the specified or selected one or more parameters of each of the concurrently-delivered time-varying first, second, and third electrical signals for thereby providing at least one of a cardioversion, defibrillation, pacing, or cardiac resynchronization stimulation energy to the biologic cardiac tissue target at the energy below the level causing permanent impact damage to the biologic cardiac tissue target.

4. The method of claim 2, further comprising determining at least one of a distance between individual ones of the electrodes or an angle formed by a geometry defined by the arrangement of the set of at least three electrodes.

5. The method of claim 4, further comprising specifying or selecting at least one of the one or more parameters based on at least one of the distance or the angle.

6. The method of claim 5, further comprising specifying or selecting at least one of the one or more parameters to normalize or otherwise adjust one or more respective phase-shifted components to obtain a desired superpositioned composite of respective phase-shifted components to provide a desired REF and using the specified or selected one or more parameters of each of the concurrently-delivered time-varying first, second, and third electrical signals for thereby providing at least one of a cardioversion, defibrillation, pacing, or cardiac resynchronization stimulation energy to the biologic cardiac tissue target at the energy below the level causing permanent impact damage to the biologic cardiac tissue target.

7. The method of claim 4, further comprising determining at least one of the distance or the angle using an impedance measurement between a pair of individual ones of the electrodes and, based upon the determining, adjusting a therapeutic electric field used for thereby providing at least one of a cardioversion, defibrillation, pacing, or cardiac resynchronization stimulation energy to the biologic cardiac tissue target at the energy below the level causing permanent impact damage to the biologic cardiac tissue target.

8. The method of claim 1, wherein the individual electrodes in the arrangement of the set of at least three electrodes that are each galvanically isolated from the biologic tissue target are located on a balloon or other cylindrical substrate that has been intravascularly introduced toward the biologic cardiac tissue target.

9. The method of claim 8, further comprising delivering the generated phase-shifted individual electrical signals to respective corresponding individual electrodes in an arrangement of a set of at least three electrodes that are each galvanically isolated from the biologic tissue target and are arranged in a circumferential ring about the balloon or other cylindrical substrate, the circumferential ring including a plurality of triads of galvanically isolated electrodes that are galvanically isolated from the biologic tissue target.

10. The method of claim 8, further comprising delivering the generated phase-shifted individual electrical signals to respective corresponding individual electrodes in an arrangement of a set of at least three electrodes that are each galvanically isolated from the biologic tissue target and are arranged longitudinally in at least one of straight linear or helical strips about the balloon or other cylindrical substrate, the strips respectively including a plurality of triads of galvanically isolated electrodes that are galvanically isolated from the biologic tissue target.

11. The method of claim 8, further comprising delivering the generated phase-shifted individual electrical signals to respective corresponding individual electrodes in an arrangement of a plurality of triads of galvanically isolated electrodes that are galvanically isolated from the biologic tissue target, each triad including a first electrode, a second electrode, and a third electrode, the plurality of triads including corresponding first electrodes arranged in a first layer on the balloon or other cylindrical substrate, corresponding second electrodes arranged in a different second layer on the balloon or other cylindrical substrate, and corresponding third electrodes arranged in a different third layer on the balloon or other cylindrical substrate, wherein the first layer, the second layer, and the third layer are electrically insulated from each other, wherein individual ones of the triads are used for thereby providing at least one of a cardioversion, defibrillation, pacing, or cardiac resynchronization stimulation energy to the biologic cardiac tissue target at the energy below the level causing permanent impact damage to the biologic cardiac tissue target.

12. The method of claim 1, wherein the individual electrodes in the arrangement of the set of at least three electrodes that are each galvanically isolated from the biologic tissue target are located on, or electrically coupled to, an implantable or wearable pulse generator for capacitively coupling the REF via the galvanically isolated electrodes toward the biologic cardiac tissue target to treat the biologic cardiac tissue target via at least one of cardioversion, defibrillation, pacing or other cardiac resynchronization.

13. The method of claim 1, wherein the individual electrodes in the arrangement include one or more intravascularly introduced galvanically isolated intracardiac electrodes.

14. The method of claim 1, wherein the individual electrodes in the arrangement include one or more subcutaneously implanted galvanically isolated electrodes coupled to a subcutaneously implanted pulse generator.

15. The method of claim 1, wherein the individual electrodes in the arrangement, include one or more wearable external galvanically isolated electrodes coupled to an external pulse generator.

16. The method of claim 1, wherein the individual electrodes in the arrangement are carried by a wearable garment and are arranged to be approximately equally spaced about a torso of a wearer of the wearable garment.

17. The method of claim 1, further comprising sensing intrinsic or evoked cardiac signals via one or more electrodes that galvanically contact the subject and, based on the sensing, controlling delivery of REF electrical field to the subject.

* * * * *